(12) United States Patent
Alizoti et al.

(10) Patent No.: US 11,464,925 B2
(45) Date of Patent: Oct. 11, 2022

(54) POSITIVE AIR PRESSURE THERAPY DEVICE, KIT AND METHODS FOR THE USE AND ASSEMBLY THEREOF

(71) Applicant: Trudell Medical International, London (CA)

(72) Inventors: Neritan Alizoti, London (CA); Luke Kilroy, London (CA); Adam Meyer, London (CA); Andreas Rifani, London (CA)

(73) Assignee: TRUDELL MEDICAL INTERNATIONAL, London (CA)

( * ) Notice: Subject to any disclaimer, the term of this patent is extended or adjusted under 35 U.S.C. 154(b) by 597 days.

(21) Appl. No.: 16/429,826

(22) Filed: Jun. 3, 2019

(65) Prior Publication Data

US 2019/0366023 A1 Dec. 5, 2019

Related U.S. Application Data

(60) Provisional application No. 62/680,239, filed on Jun. 4, 2018.

(51) Int. Cl.
*A61M 16/00* (2006.01)
*A61M 16/20* (2006.01)

(52) U.S. Cl.
CPC .... *A61M 16/0012* (2014.02); *A61M 16/0057* (2013.01); *A61M 16/208* (2013.01); *A61M 2205/3331* (2013.01); *A61M 2205/42* (2013.01)

(58) Field of Classification Search
CPC .............. A61M 16/00; A61M 16/0012; A61M 16/0051; A61M 16/0069; A61M 16/022;
(Continued)

(56) References Cited

U.S. PATENT DOCUMENTS 1,479,714 A * 1/1924 Herdle ...................... F01N 1/14
181/263
2,218,063 A * 10/1940 Munzer ................... F01N 1/083
181/275
(Continued)

FOREIGN PATENT DOCUMENTS

CA 2 812 240 A1 4/2012
CN 105816945 A 8/2016
(Continued)

OTHER PUBLICATIONS

International Search Report and Written Opinion for International Application No. PCT/IB2019/054578 dated Oct. 3, 2019 (11 pgs).

*Primary Examiner* — Annette Dixon
(74) *Attorney, Agent, or Firm* — Crowell & Moring LLP

(57) ABSTRACT

A positive air pressure delivery device includes a housing having an inhalation inlet, an inhalation outlet, and an interior cavity in fluid communication with the inhalation inlet and outlet. A pressurized fluid inlet includes an outlet orifice in fluid communication with the interior cavity between the inhalation inlet and outlet. A sound reducer baffle has a convex dome surface positioned downstream of and facing the outlet orifice in a spaced apart relationship therewith. One embodiment of the housings includes a body, an end cap and a baffle insert. In various embodiments, the positive air pressure delivery device may be used in combination with other therapy devices, including an OPEP and pressure indicator. A kit and method of using the device are also provided.

37 Claims, 23 Drawing Sheets

(58) Field of Classification Search
CPC ............ A61M 16/0875; A61M 16/104; A61M 16/107; A61M 16/202; A61M 16/206; A61M 16/208; A61M 16/209; A61M 2016/0039; A61M 2016/0042; F01N 1/08; F01N 1/083; F01N 1/14; F01N 1/165; F15D 1/02; G01F 15/00; G01F 15/04; Y10S 181/403; Y10S 55/30; Y10T 137/86413

See application file for complete search history.

(56) References Cited

U.S. PATENT DOCUMENTS

| | | | |
|---|---|---|---|
| 3,351,092 A | | 11/1967 | Ingerfield et al. |
| 3,467,092 A | * | 9/1969 | Bird .................. A61M 16/0012 128/204.25 |
| 3,806,039 A | | 4/1974 | Mocarski |
| 4,190,045 A | | 2/1980 | Bartels |
| 4,261,355 A | | 4/1981 | Glazener |
| 4,270,577 A | * | 6/1981 | Brown ..................... F15D 1/02 138/39 |
| 5,018,517 A | | 5/1991 | Liardet |
| 5,036,847 A | | 8/1991 | Boussignac et al. |
| 5,040,532 A | | 8/1991 | Alfrey |
| 5,402,938 A | | 4/1995 | Sweeney |
| 5,605,148 A | | 2/1997 | Jones |
| 6,030,353 A | | 2/2000 | Van Brunt |
| 6,253,766 B1 | | 7/2001 | Niles et al. |
| 6,581,598 B1 | | 6/2003 | Foran et al. |
| 6,776,159 B2 | | 8/2004 | Pelerossi et al. |
| 7,059,324 B2 | | 6/2006 | Pelerossi et al. |
| 7,360,537 B2 | | 4/2008 | Snyder et al. |
| 7,779,841 B2 | | 8/2010 | Dunsmore et al. |
| 8,025,054 B2 | | 9/2011 | Dunsmore et al. |
| 8,029,244 B2 | | 10/2011 | Dumas et al. |
| 8,225,785 B2 | | 7/2012 | Richards et al. |
| 8,251,876 B2 | | 8/2012 | Boerst et al. |
| 8,327,849 B2 | | 12/2012 | Foley et al. |
| 8,485,179 B1 | | 7/2013 | Meyer et al. |
| 8,534,284 B2 | | 8/2013 | Dunsmore et al. |
| 8,528,547 B2 | | 9/2013 | Dunsmore et al. |
| 8,539,951 B1 | | 9/2013 | Meyer et al. |
| 8,567,400 B2 | | 10/2013 | Mansour et al. |
| 8,677,999 B2 | | 3/2014 | Allum et al. |
| 9,180,271 B2 | | 11/2015 | Guo et al. |
| 9,205,217 B2 | | 12/2015 | Richards et al. |
| 9,358,417 B2 | | 6/2016 | Meyer et al. |
| 9,517,315 B2 | | 12/2016 | Meyer et al. |
| 9,849,257 B2 | | 12/2017 | Meyer et al. |
| 2003/0172931 A1 | * | 9/2003 | Kerechanin, II ...... A61M 16/00 128/204.18 |
| 2003/0234017 A1 | | 12/2003 | Pelerossi et al. |
| 2007/0056587 A1 | | 3/2007 | Travan |
| 2007/0113852 A1 | | 5/2007 | Martin |
| 2008/0110451 A1 | | 5/2008 | Dunsmore et al. |
| 2008/0245368 A1 | | 10/2008 | Dunsmore et al. |
| 2010/0180899 A1 | | 7/2010 | Capezzuto |
| 2010/0307487 A1 | | 12/2010 | Dunsmore et al. |
| 2012/0097164 A1 | | 4/2012 | Rozario et al. |
| 2012/0138052 A1 | | 6/2012 | Hearn et al. |
| 2012/0272956 A1 | | 11/2012 | Rusher |
| 2014/0150801 A1 | | 6/2014 | Rusher |
| 2015/0224269 A1 | | 8/2015 | Alizoti et al. |
| 2017/0072159 A1 | | 3/2017 | Romano et al. |
| 2017/0136205 A1 | | 5/2017 | Rusher |
| 2017/0157346 A1 | | 6/2017 | Bennett et al. |
| 2017/0319800 A1 | | 11/2017 | Richards |
| 2018/0008789 A1 | | 1/2018 | Alizoti et al. |
| 2018/0161531 A1 | | 6/2018 | Costella et al. |

FOREIGN PATENT DOCUMENTS

| | | |
|---|---|---|
| CN | 106345025 A | 1/2017 |
| CN | 205948145 U | 2/2017 |
| EP | 0 290 062 A2 | 11/1988 |
| EP | 1 078 646 A2 | 2/2001 |
| EP | 1 772 165 A1 | 4/2007 |
| EP | 2 444 114 A1 | 4/2012 |
| EP | 1 908 489 A1 | 1/2017 |
| GB | 971953 | 10/1964 |
| GB | 2 160 108 A | 12/1985 |
| GB | 2 169 192 A | 7/1986 |
| GB | 2 448 212 A | 10/2008 |
| WO | WO 03/026730 A1 | 4/2003 |
| WO | WO 2008/101302 A1 | 8/2008 |
| WO | WO 2009/067554 A1 | 5/2009 |
| WO | WO 2016/075426 A1 | 5/2016 |

* cited by examiner

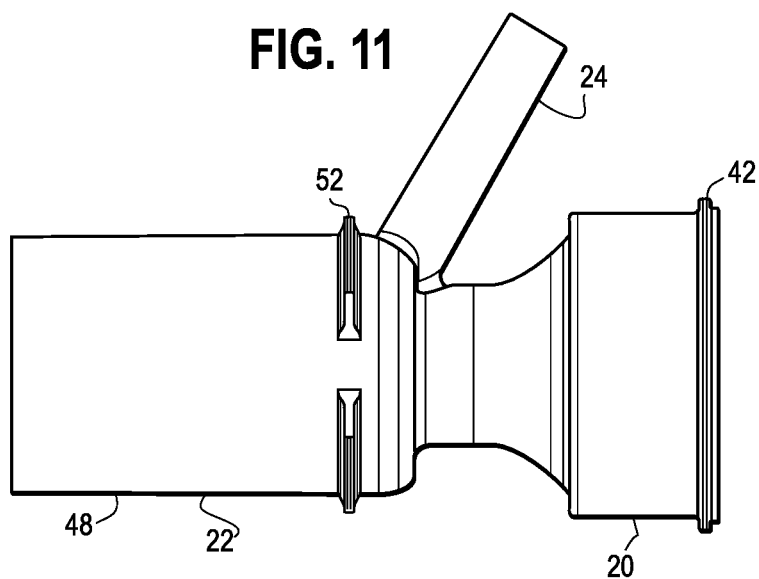
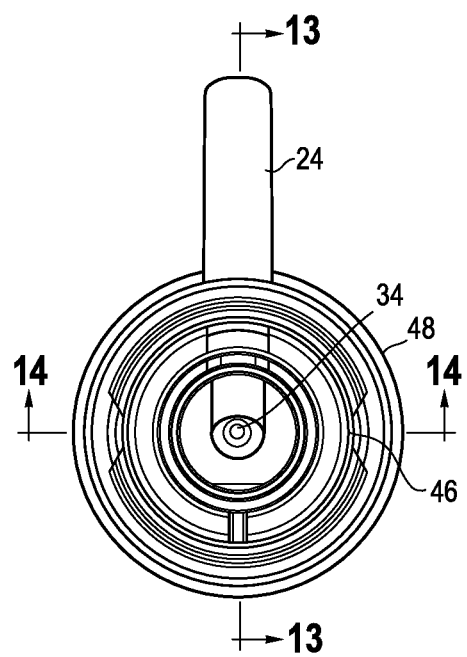

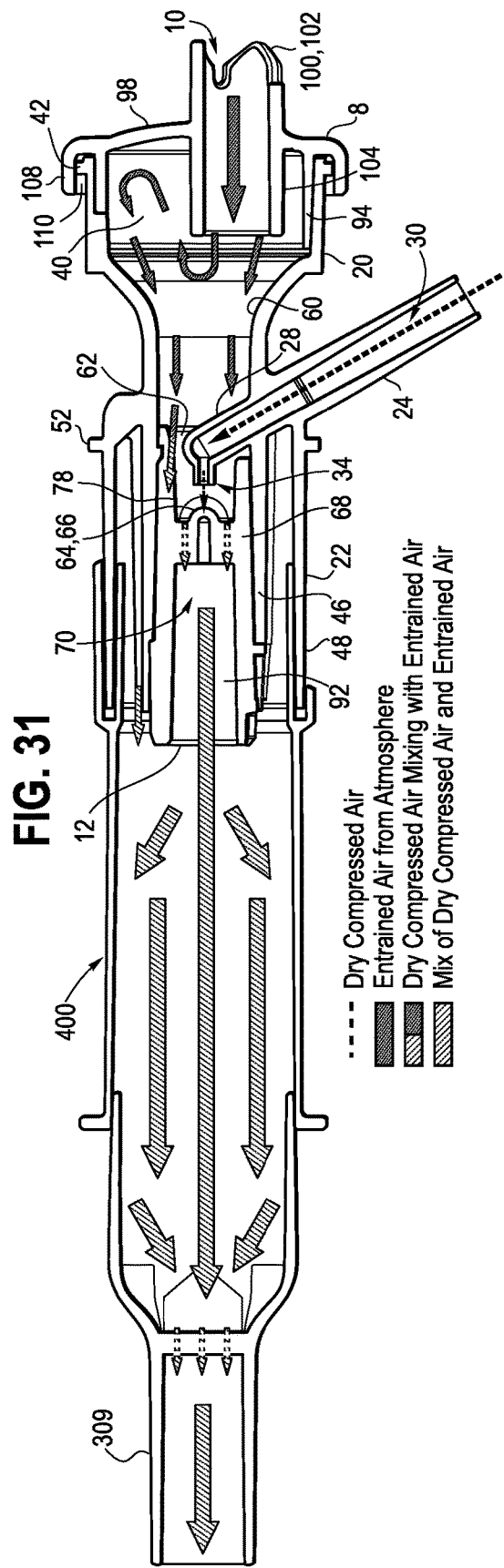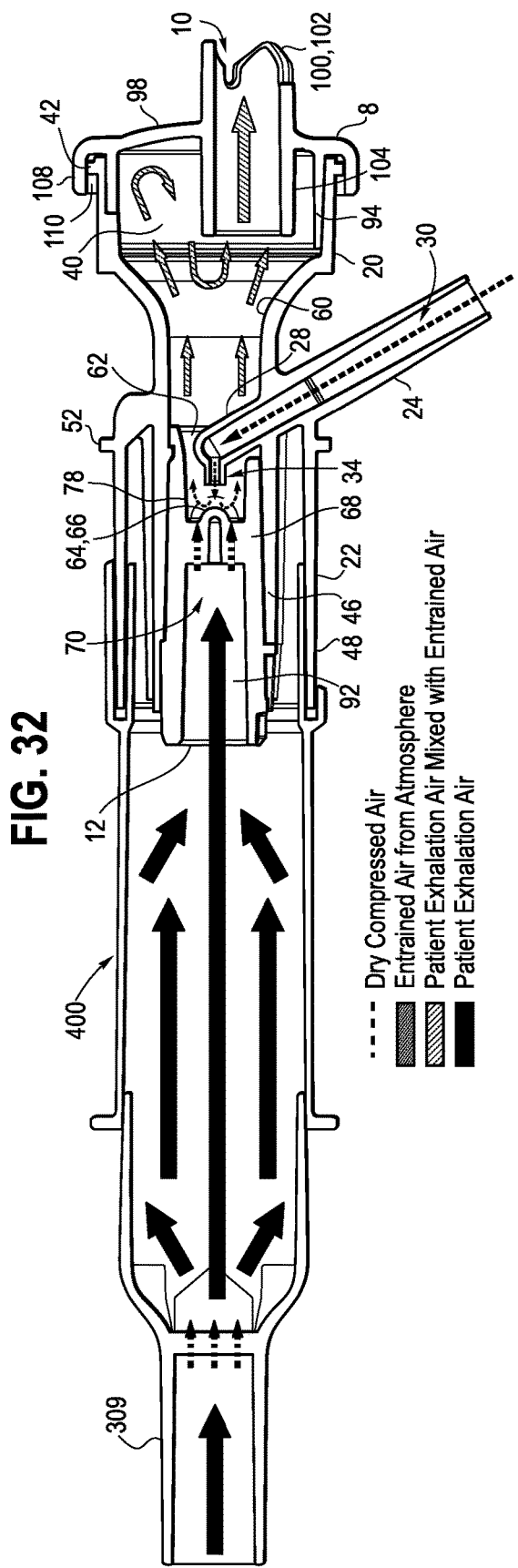

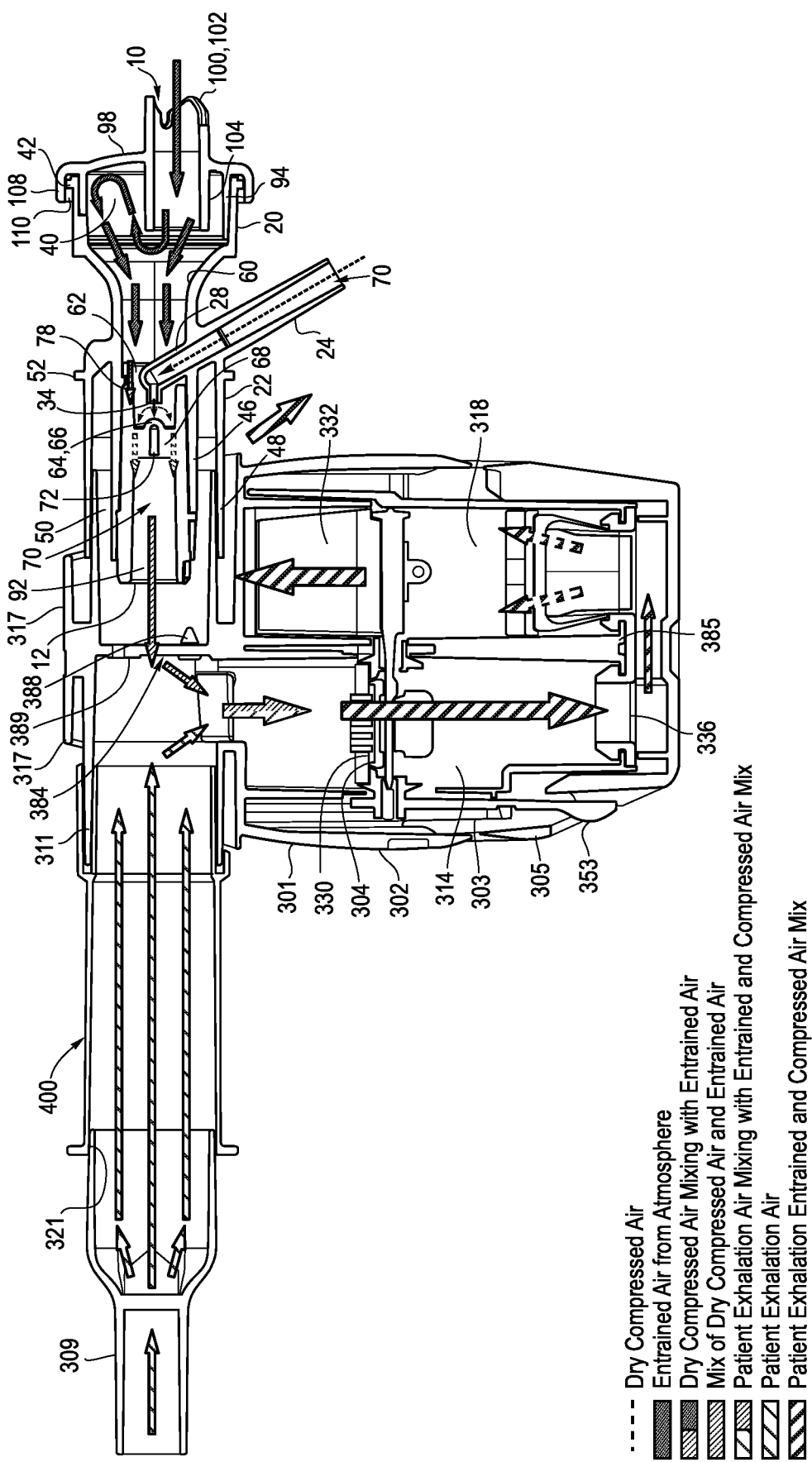

POSITIVE AIR PRESSURE THERAPY DEVICE, KIT AND METHODS FOR THE USE AND ASSEMBLY THEREOF

This application claims the benefit of U.S. Provisional Application No. 62/680,239, filed Jun. 4, 2018, the entire disclosure of which is hereby incorporated herein by reference.

TECHNICAL FIELD

The present invention relates generally to a therapy device, including a positive air pressure therapy device, and also to kits and methods of delivering a positive air pressure.

BACKGROUND

It is well known to use positive air pressure (PAP) devices to supply supplemental oxygen and/or air to the lungs of a patient. Known expiratory pressure devices, such as positive expiratory pressure devices, may also help prevent lung collapse and increase airflow by providing resistance to the patient exhalation pathway. PAP devices have been used in combination with other devices, including oscillating positive expiratory pressure devise (OPEP). In some combinations, air may escape to the ambient or atmosphere through one or more of the various devices, which may introduce a therapy pressure drop, a louder device and potential contamination to the surrounding environment.

SUMMARY

Briefly stated, in one aspect, one embodiment of a positive air pressure delivery device includes a housing having an inhalation inlet, an inhalation outlet, and an interior cavity in fluid communication with the inhalation inlet and outlet. A pressurized fluid inlet includes an outlet orifice in fluid communication with the interior cavity between the inhalation inlet and outlet. A sound reducer baffle has a convex dome surface positioned downstream of and facing the outlet orifice in a spaced apart relationship therewith.

In another aspect, one embodiment of a positive air pressure assembly kit includes a body having an inlet end, an outlet end and an interior cavity in fluid communication with the inlet and outlet ends. A pressurized fluid inlet includes an outlet orifice in fluid communication with the interior cavity between the inlet and outlet ends. An end cap is adapted to be coupled to the inlet end. The end cap defines an inhalation inlet adapted to open into the interior cavity. A baffle insert is adapted to be coupled to the outlet end. The baffle insert includes a sound reducer baffle having a convex dome surface adapted to be positioned downstream of and facing the outlet orifice in a spaced apart relationship therewith when the baffle insert is coupled to the inlet end. The baffle insert further includes an inhalation outlet.

In one embodiment, the end cap may be configured with muffler features. In addition, the inhalation inlet and outlet may not be co-axial, which provides for a tortuous path, and may increase the expiratory pressure while also reducing the overall noise level of the device. In addition, in one embodiment, the outlet orifice is formed as a one-piece unit, which can improve the performance of the unit by eliminating manufacturing variability and tolerance build-up.

A method of administering a positive air pressure to a user includes passing air through an inhalation inlet of a housing into an interior cavity of the housing, introducing a pressurized fluid into the interior cavity through an outlet orifice of a pressurized fluid inlet, impacting a convex dome surface of a sound reducer baffle with the pressurized fluid, wherein the convex dome surface is positioned downstream of and facing the outlet orifice in a spaced apart relationship therewith, and passing the air and the pressurized fluid through an inhalation outlet.

In various embodiments, the positive air pressure device is configured and adapted to be used alone, or to be coupled to other therapy devices, including for example and without limitation an oscillating positive expiratory pressure device (OPEP) and/or a pressure detecting device (pressure indicator), such as a manometer.

The various aspects and embodiments provide significant advantages over other positive air pressure devices and systems. For example and without limitation, the geometry of the housing, including the body and baffle insert, by way of a multiplier area and venture geometry, accelerate the inhaled air flow. At the same time, the sound reducer baffle, alone or in combination with an end cap muffler, orifice construction and/or flow path, reduce the associated noise of the air flow through the housing. Since the device is used close to the face of the patient, the reduced sound level can improve the user's experience, and reduce the level of annoyance to others near the patient, such as caregivers.

The present embodiments of the invention, together with further objects and advantages, will be best understood by reference to the following detailed description taken in conjunction with the accompanying drawings.

BRIEF DESCRIPTION OF THE DRAWINGS

FIG. 11 is a side view of a body component of the positive air pressure therapy device shown in FIG. 6.

FIG. 12 is an end view of the body component of the positive air pressure therapy device shown in FIG. 11.

FIG. 31 is a cross-sectional view of the positive air pressure therapy device during inhalation.

FIG. 32 is a cross-sectional view of the positive air pressure therapy device during exhalation when not used in combination with OPEP.

FIG. 34 is a cross-sectional view of the positive air pressure therapy device during exhalation when used in combination with OPEP.

DETAILED DESCRIPTION OF THE PRESENTLY PREFERRED EMBODIMENTS

General

Figure 1:
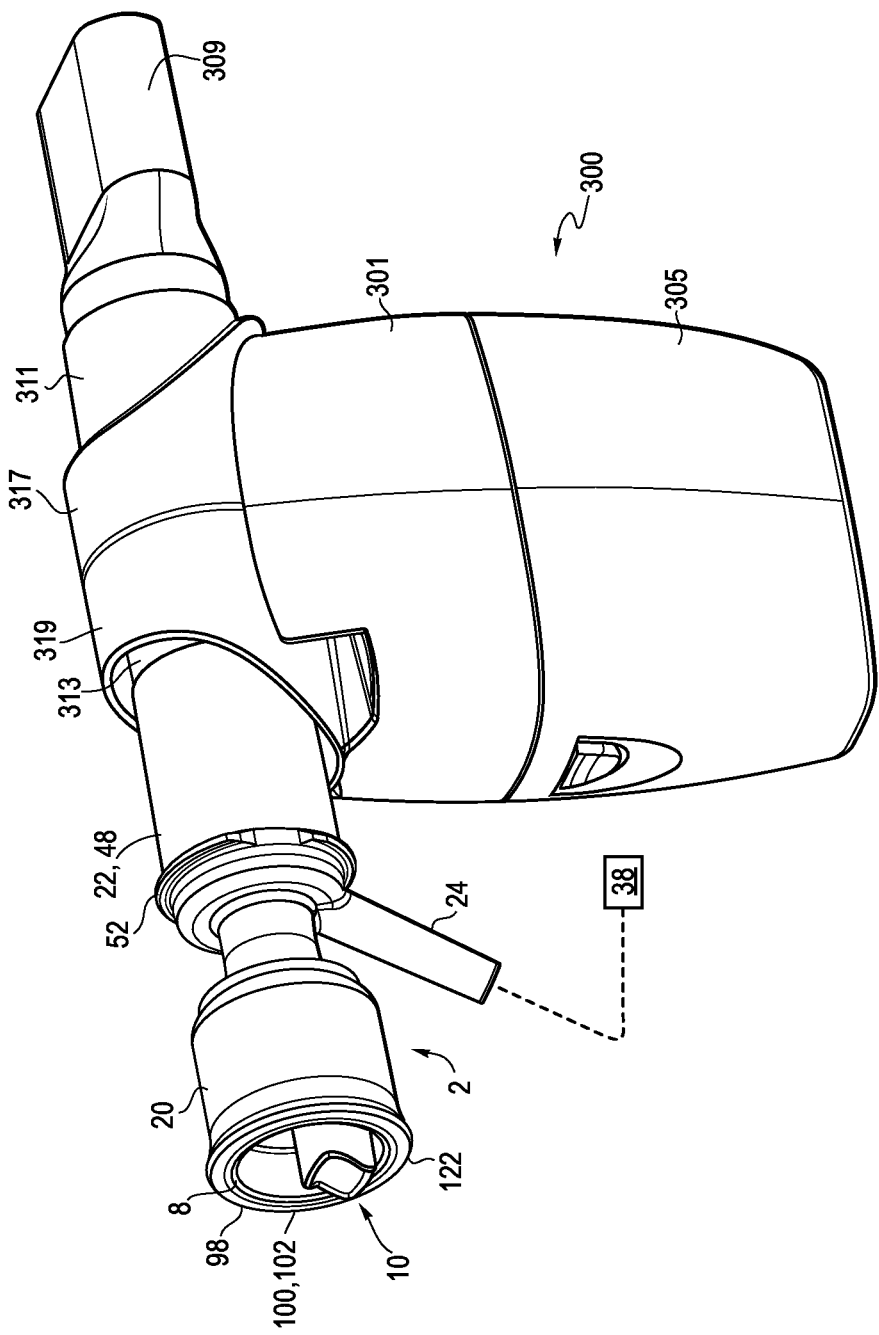
FIG. 1 is a perspective view of one embodiment of a positive air pressure therapy device coupled to an oscillating positive expiratory pressure device.

It should be understood that the term "plurality," as used herein, means two or more. The term "coupled" and "secured" means connected to or engaged with, whether directly or indirectly, for example with an intervening member, and does not require the engagement to be fixed or permanent, although it may be fixed or permanent. It should be understood that the use of numerical terms "first," "second," "third," etc., as used herein does not refer to any particular sequence or order of components; for example "first" and "second" tubular components may refer to any sequence of such members, and is not limited to the first and second components of a particular configuration unless otherwise specified. It should be understood that the terms "inlet" and "outlet" during an inhalation phase may serve the opposite function ("outlet" and "inlet" respectively) during an exhalation phase, such that, for example, an inhalation inlet may also define an exhalation outlet and an inhalation outlet may also define an exhalation inlet. The term "longitudinal" as used herein means a lengthwise direction, for example between the inhalation inlet and outlet.

Referring to FIGS. 1-4, various therapy systems or assemblies include a combination of two or more therapy devices, including for example a positive air pressure delivery (PAP) device 2, a pressure indicator 400, including a manometer, and/or an oscillating positive expiratory pressure (OPEP) device 300.

OPEP Device

The OPEP device 300 includes a housing 302 having a front section 301, a rear section 305, and an inner casing 303, which may be separable so that the components contained therein can be periodically accessed, cleaned, replaced, or reconfigured, as required to maintain the ideal operating conditions. For example, the front section 301 and the rear section 305 of the housing 302 may be removably connected via a snap fit engagement. The OPEP device 300 also includes a mouthpiece 309, an inhalation port 311, a one-way valve 384 disposed therebetween, an adjustment mechanism 353, a restrictor member 330, a vane 332, and a variable nozzle 336.

The inner casing 303 is configured to fit within the housing 302 between the front section 301 and the rear section 305, and partially defines a first chamber 314 and a second chamber 318. A first chamber outlet and a second chamber outlet are formed within the inner casing. One end 385 of the inner casing 303 is shaped and configured to receive the variable nozzle 336 and maintain the variable nozzle 336 between the rear section 305 and the inner casing 303.

In general, the one-way valve 384 comprises a post 368 adapted for mounting in the front section 301 of the housing 302, and a flap 389 adapted to bend or pivot relative to the post 388 in response to a force or a pressure on the flap 389. Those skilled in the art will appreciate that other one-way valves may be used in this and other embodiments described herein without departing from the teachings of the present disclosure. The one-way valve 384 may be positioned in the housing 302 between the mouthpiece 309 and the inhalation port 311.

The OPEP device 300 may include an adjustment mechanism 353 adapted to change the relative position of a chamber inlet 304 with respect to a housing 302 and a restrictor member 330, which in turn changes the range of rotation of a vane 332 operatively connected thereto. A user is therefore able to conveniently adjust both the frequency and the amplitude of the OPEP therapy administered by the OPEP device 300 without opening the housing 302 and disassembling the components of the OPEP device 300. The administration of OPEP therapy using the OPEP device 300 is otherwise the same as described above with regards to the OPEP device 100.

Figure 2:
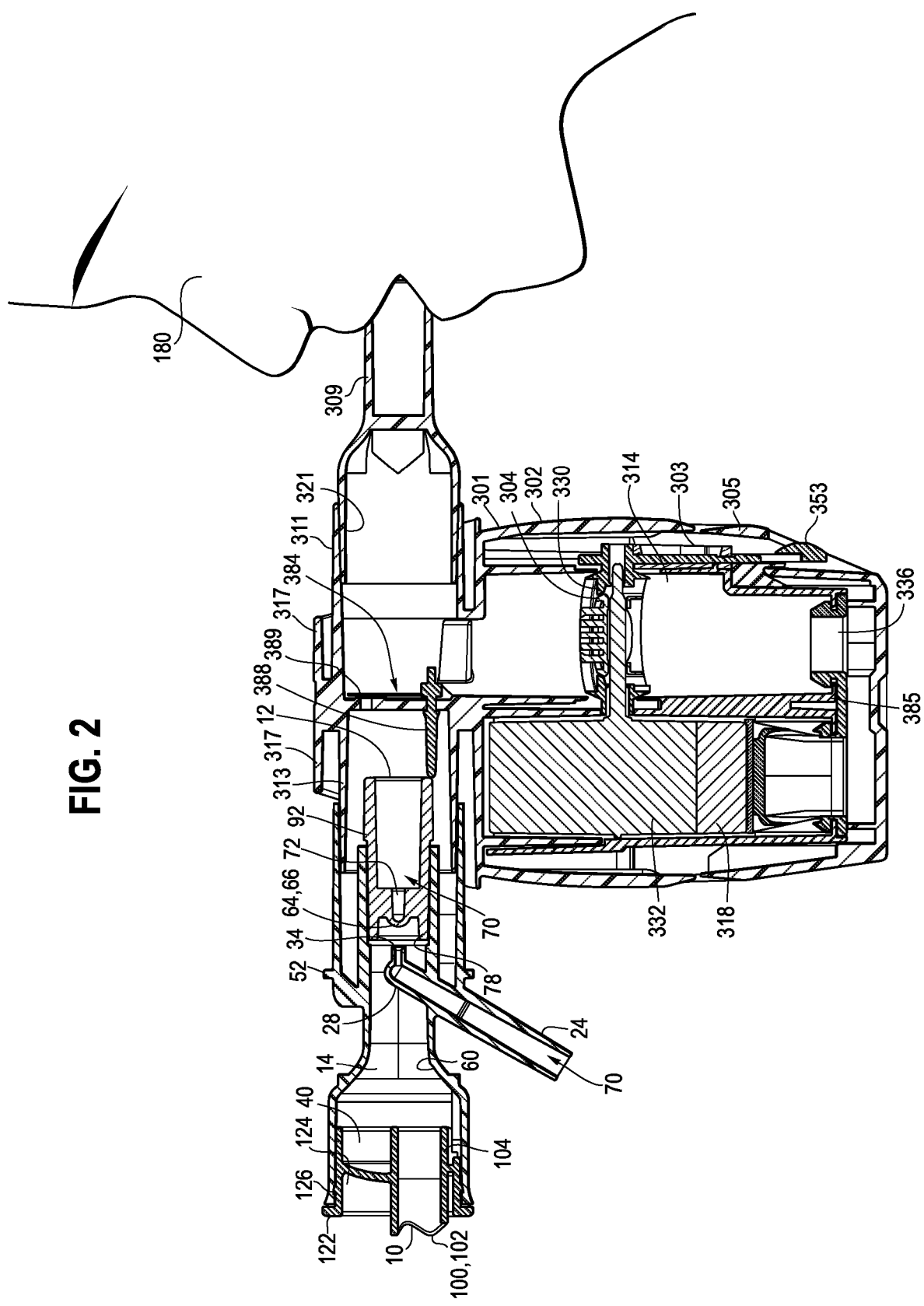
FIG. 2 is a cross-sectional view of one embodiment of a positive air pressure therapy device coupled to an oscillating positive expiratory pressure device.

The OPEP device 300 may be adapted for use with other or additional interfaces, such as an aerosol delivery device. In this regard, the OPEP device 300 is equipped with an inhalation port 311 in fluid communication with the mouthpiece 309 and an inlet port 313, configured as a first tubular portion, with a second tubular portion surrounding at least a portion of the inlet port. The inhalation port, as shown in FIG. 2, is configured as a first tubular portion, with a second tubular portion 317 surrounding at least a portion of the first tubular portion. The mouthpiece 309 is coupled to the inhalation port 311. A tubular portion 321 of the mouthpiece 309 is inserted into and engages an interior of the inhalation port 311, also configured as a tubular portion, for example with a friction fit. As noted above, the inhalation port may include a separate one-way valve 384 configured to permit a user of the OPEP device 300 both to inhale the surrounding air from the inlet port 313 through the one-way valve 384 and to exhale through the chamber inlet 304, without withdrawing the mouthpiece 309 of the OPEP device 300 between periods of inhalation and exhalation. In addition, the aforementioned commercially available aerosol delivery devices may be connected to the inhalation port 311 for the simultaneous administration of aerosol therapy (upon inhalation) and OPEP therapy (upon exhalation).

The front section 301, the rear section 305, and the inner casing 303 are assembled to form a first chamber 314 and a second chamber 318. An exhalation flow path 310 is defined between the mouthpiece 309 and at least one of the first and second chamber outlets, both of which are formed within the inner casing. As a result of the inhalation port 311 and the one-way valve 348, the exhalation flow path 310 begins at the mouthpiece 309 and is directed toward the chamber inlet 304, which in operation may or may not be blocked by the restrictor member 330. After passing through the chamber inlet 304, the exhalation flow path 310 enters the first chamber 314 and makes a 180° turn through the variable nozzle 336. After passing through an orifice of the variable nozzle 336, the exhalation flow path enters the second chamber 318, in the second chamber 318, the exhalation flow path may exit the second chamber 318, and ultimately the housing 302, through at least one of the first or second chamber outlets. Those skilled in the art will appreciate that the exhalation flow path is exemplary, and that air exhaled into the OPEP device 300 may flow in any number of directions or paths as it traverses from the mouthpiece 309 or chamber inlet 304 to the chamber outlet(s).

Various suitable pressure indicators and OPEP devices, and combinations thereof, are disclosed in U.S. Publication No. 2015/0224269A1, assigned to Trudell Medical International, the Assignee of the present application, the entire disclosure of which is hereby incorporated herein by reference. The pressure indicator embodiments described herein provide an ergonomic pressure indicator that is easily integrated with existing OPEP devices, and is suitable for repeated use by a single patient. Furthermore, these embodiments are configured to minimize oscillations in the visual feedback provided to the user, therefore allowing the pressure indicator to display a readable pressure level, and at the same time, provide dynamic visual feedback to the let user know that the OPEP device is working by sensing its oscillating pressures.

Pressure Indicator

It should be understood that the pressure indicator embodiments disclosed and/or incorporated by reference herein are shown and described for use with the OPEP device 300 of FIGS. 1 and 2. It should be appreciated that the pressure indicators are also suitable for use with other OPEP devices, including for example: other OPEP embodiments described herein; those shown and described in U.S. Pat. Nos. 5,018,517; 6,581,598; 6,776,159; 7,059,324; 8,327,849; 8,539,951; and 8,485,179, the entireties of which are hereby incorporated herein by reference; those shown and described in U.S. patent application Ser. Nos. 13/489,894 and 14/092,091, the entireties of which are hereby incorporated herein by reference; and, any number of commercially available OPEP devices, such as the AEROBIKA® OPEP from Trudell Medical International of London, Canada, the ACAPELLA® OPEP from Smiths Medical of St. Paul, Minn., the FLUTTER® OPEP from Axcan Scandipharm Inc. of Birmingham, Ala., and the RC-CORONET® OPEP from Curaplex of Dublin, Ohio.

Referring to FIGS. 3, 4, 9 and 10, a first embodiment of a pressure indicator 400 includes a body 402, a conduit 404 extending from the body 402, a plug 406 positioned along and inserted into the conduit 404, and an instrument for measuring pressure in the form of a manometer 408 positioned at an outlet of the conduit 404.

Figure 3:
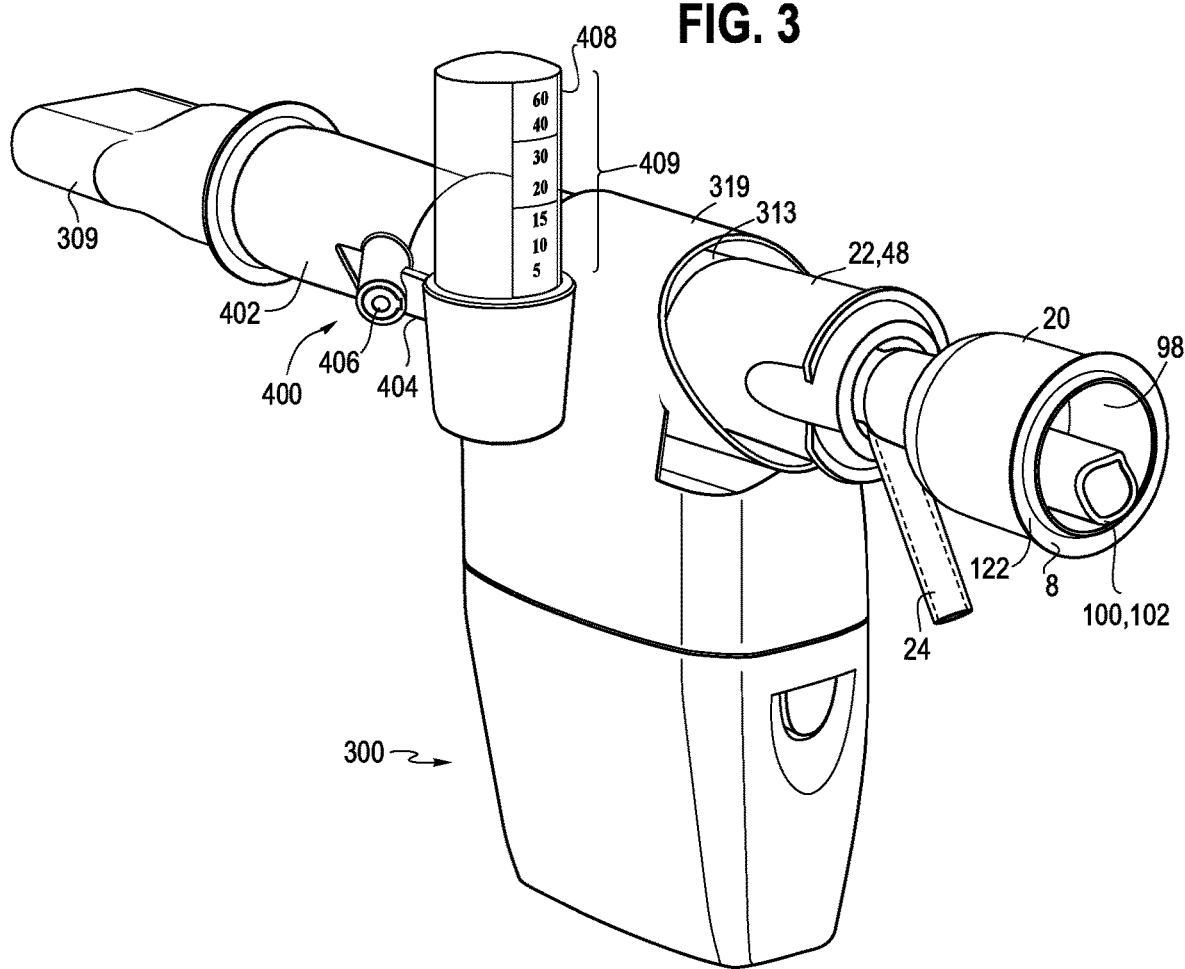
FIG. 3 is a perspective view of one embodiment of a positive air pressure therapy device coupled to an oscillating positive expiratory pressure device and manometer.
Figure 9:
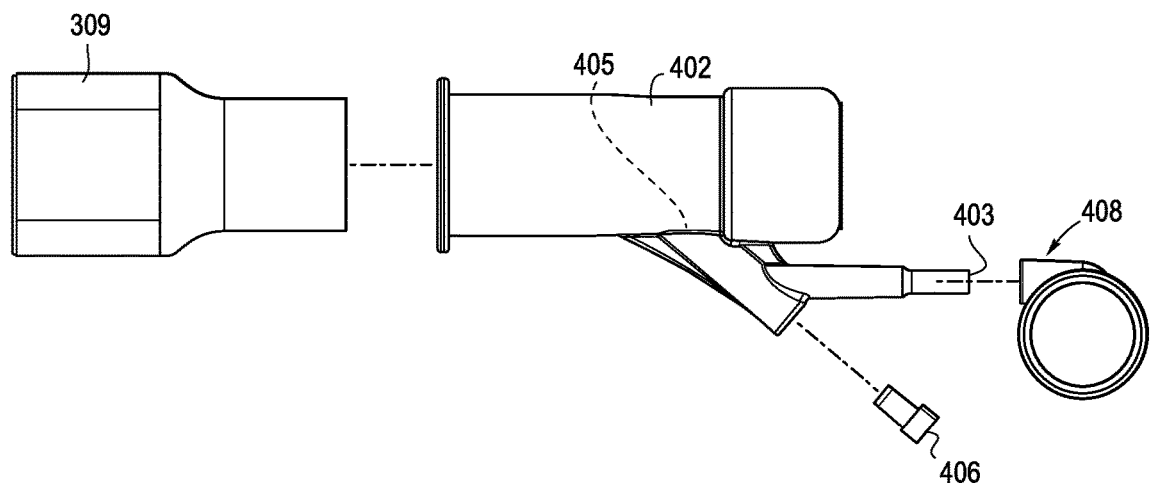
FIG. 9 is a top view of a manometer assembly.

The body 402 may be sized and shaped for integration with existing OPEP devices, for example, as shown in FIGS. 3 and 9, with the mouthpiece 309 of the OPEP device 300. In this example, the body 402 is comprised of 22 mm ISO male/female conical connectors shaped and sized to connect to the mouthpiece 309 of the OPEP device 300.

Extending from the body 402 is a conduit 404 configured to transmit a pressure from within the OPEP device 300 to the manometer 408. An inlet 405 permits a pressure within the body 402 to pass into the conduit 404. As shown, the conduit 404 extends away from the body 402, then angles alongside the OPEP device 300, thereby maintaining the portability and ergonomics of the OPEP device 300, and avoiding the need for lengthy tubing or additional attachments.

The manometer 408 is positioned at an outlet 403 of the conduit 404. It should be appreciated, however, that a portion of the conduit 404 could extend into a passageway in the manometer 408, or other instrument for measuring pressure. The manometer 408 may be a piston-type gauge such as, for example, an AMBU® Disposable Pressure Manometer from Ambu A/S of Copenhagen, Denmark. Other instruments for measuring pressure may also be used in place of the manometer 408. In general, the manometer 408 includes a spring-loaded piston that moves an indicator within the piston in response to a change in pressure. Preferably, the instrument for measuring pressure may comprise one or more of a numerical, color, shape, or other visual indicia, or one or more of a sound or other auditory indicia, or a combination of one or more of each of a visual indicia and an auditory indicia. In one exemplary embodiment, the manometer 408 includes a numerical indicia 409 of pressures measured by the manometer 408. Preferably, the instrument for measuring pressure is positioned relative to the respiratory treatment device such that the indicator and indicia are visible to the user during treatment. For example as shown in FIG. 3, the manometer 408 is positioned relative to the respiratory treatment device in the form of an OPEP device 300 such that the indicator and indicia 409 are viewable to a user of the OPEP device 300 during treatment.

The plug 406 is insertable by press-fitting along the conduit 404 at a point where the conduit 404 angles alongside the OPEP device 300. In one embodiment, the plug may not be removed, but may be made of a self-sealing material, such as a silicone material, allowing a needle or other similar instrument to be inserted and removed for cleaning purposes while maintaining a seal. In another embodiment, the plug may be periodically removed for cleaning of the pressure indicator 400. The plug 406 may include a cutout that may be aligned with a passage in the conduit 404. When the plug 406 is inserted into the conduit 404 such that the cutout is partially or completely aligned with the passage, a pressure stabilizing orifice is formed in the conduit 404. The pressure stabilizing orifice is configured to dampen oscillations in the pressures transmitted from the OPEP device 300 to the manometer 408.

During administration of OPEP therapy, an oscillating back pressure is transmitted to the user of the OPEP device, which is received by the user at the mouthpiece. When the pressure indicator 400 is connected to such an OPEP device, for example the OPEP device 300, the oscillating pressure is transmitted from within the body 402 to the manometer 408 through the conduit 404. The oscillations in the pressure are dampened, however, by the pressure stabilizing orifice, as the flow of air along the conduit 404 through the pressure stabilizing orifice is restricted. After the pressure has been dampened by the pressure stabilizing orifice, it is received and measured by the manometer 408, which in turn provides the user with a visual indication of the pressure achieved during administration of OPEP therapy. This allows the user or caregiver to monitor the treatment regimen or therapy to ensure that the appropriate pressures are achieved for the prescribed period of time. In some instances, a treatment regimen or therapy alternating between exhalation at a high pressure for a predetermined period of time and exhalation at a low pressure for a predetermined period of time may be desirable. A visual or auditory indication of the pressure achieved during treatment will allow the user or caregiver to determine the level of compliance with the prescribed treatment regimen or therapy.

As previously noted, the pressure indicator embodiments described herein may be used with other OPEP devices, including for example: an ACAPELLA® OPEP device from Smiths Medical of St. Paul, Minn.; a FLUTTER® OPEP device from Axcan Scandipharm Inc. of Birmingham, Ala.; and, an RC-CORONET® OPEP device 830 from Curaplex of Dublin, Ohio.

PAP Device

Referring to FIGS. 1-3, 14 and 15, various embodiments of a positive air pressure (PAP) delivery device 2 are shown. In one embodiment, the PAP device includes a housing having a body 4, a baffle insert 6 and an end plug 8. It should be understood that in other embodiments, various features of one or both of the baffle insert and/or end plug may be integrally formed with the body.

In one embodiment, the housing, whether formed as a single unitary member or as an assembly of two or more components, includes an inhalation inlet 10, an inhalation outlet 12 and an interior cavity 14 disposed between and in fluid communication with the inhalation inlet and outlet. It should be understood that the interior cavity is defined as the space providing fluid communication between the inhalation inlet and outlet, regardless of whether that space is defined by the body, end cap and/or baffle insert. The inhalation outlet defines a first longitudinal axis 16 in alignment with the interior cavity, while the inhalation inlet defines a second longitudinal axis 18 that is spaced apart a distance D from the first longitudinal axis, with the first and second longitudinal axes being parallel in one embodiment. It should be understood that the first and second longitudinal axes may not be parallel in other embodiments, or may alternatively be co-axial. The inhalation inlet 10 and outlet 12 are defined respectively by the end cap 8, or plug, and baffle insert 6 in one embodiment, with various portions of the interior cavity defined by each of the end cap, body and baffle insert. The end cap 8, or plug, is coupled to an inlet end 20 of the housing body, while the baffle insert is coupled to an outlet end 22 of the body. The end plug and/or baffle insert may be releasably coupled to the body. Alternatively, the end plug and/or baffle insert may be fixedly secured to the body, meaning those components are not intended to be separated from the body under normal conditions, for example in the absence of excessive force that may damage the components.

A pressurized fluid inlet 24 also is coupled to the body 4, and is integrally formed therewith in one embodiment, meaning the fluid inlet, including the orifice outlet, is one-piece. The one-piece configuration ensures a more consistent pressure performance, as variances in molding and tolerances in assembly are eliminated.

Figure 21:
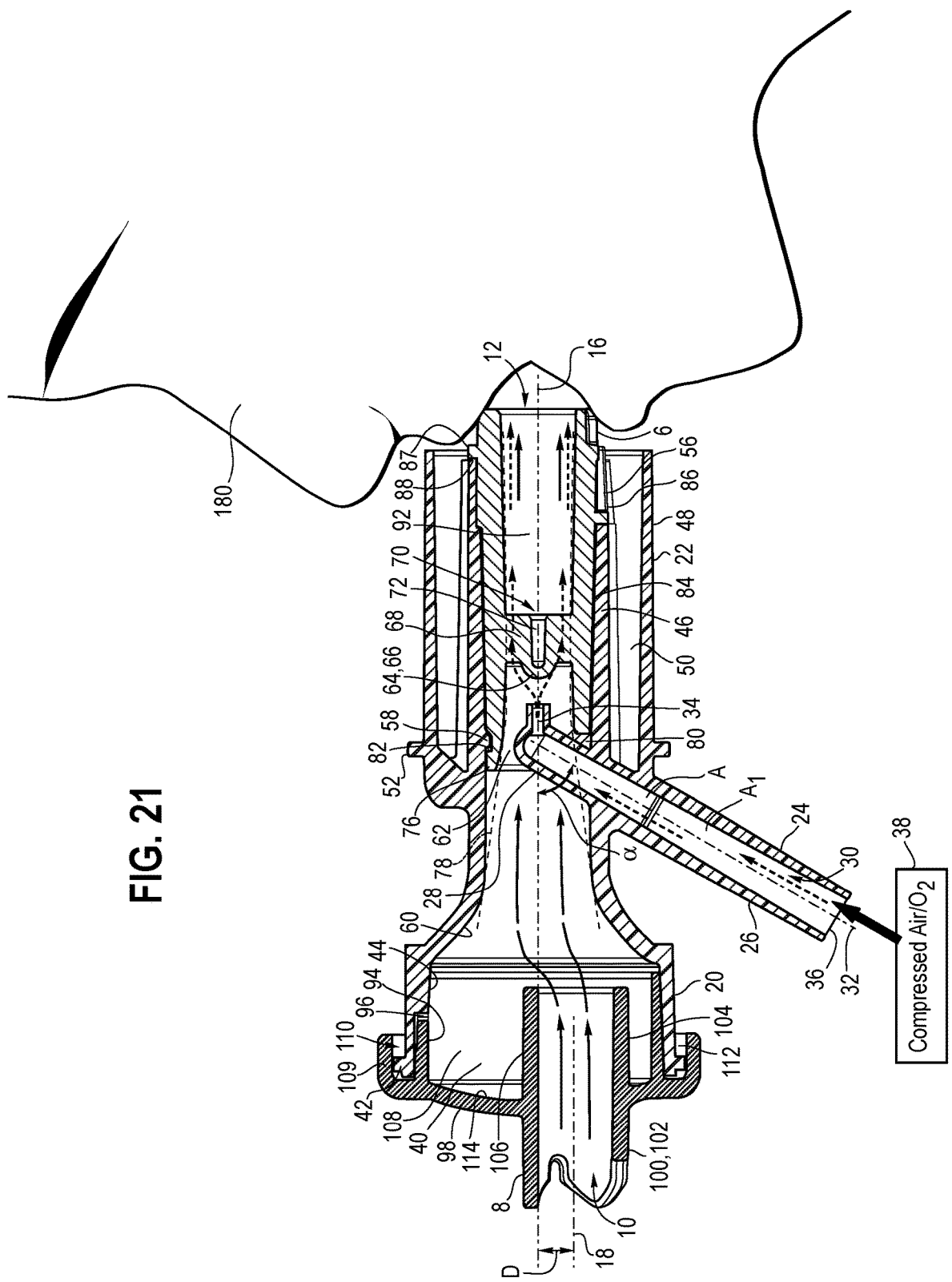
FIG. 21 is a cross-sectional view of the positive air pressure therapy device during inhalation.

The fluid inlet has a tubular portion 26 extending outwardly from an exterior surface of the body in an upstream direction toward the inhalation inlet and away from the inhalation outlet. The fluid inlet also has a head portion 28 extending inwardly from an interior surface of the body in a downstream direction toward the inhalation inlet and away from the inhalation outlet tubular portion. The tubular portion and head portion define a flow channel 30, which is linear in one embodiment and defines a flow axis 32 forming an angle α relative to the first longitudinal axis 16. The flow channel may be constricted from a first cross-sectional area A1 to a second cross sectional area A2 as shown in FIG. 21. The head portion defines an outlet orifice 34 in fluid communication with the interior cavity between the inhalation inlet and outlet. The outlet orifice 34 is aligned with the first longitudinal axis 16 and is oriented downstream toward the inhalation outlet 12 of the housing. The term "downstream" refers to a direction travelling from the inhalation inlet 10 to the inhalation outlet 12, or the direction of fluid flow from the inlet to the outlet during inhalation. The term "upstream" refers to a direction opposite "downstream." In one embodiment, the outlet orifice 34 has a diameter of about 1.23 mm±0.04 mm. Flow from the outlet orifice is 1.73±0.12 liter per minute (LPM) at 0.15±0.02 PSI. A distal end, or fluid port 36, of the fluid inlet may be coupled to a fluid supply source 38, for example a compressed air or oxygen supply, which may include in various embodiments a pressure tank of fluid, a pump and/or compressor. The supply source 38 may be coupled to the fluid port with a tube that is received interiorly in A1, or exteriorly around the tubular portion 26.

The inlet end of the housing body is enlarged, with a portion of the interior cavity 14 at the inlet end defining an expansion chamber 40. In one embodiment, the expansion chamber is substantially cylindrical, with an inner surface that is slightly inwardly tapered, for example from a first inner diameter of 26.91 mm to a second inner diameter of 26.34 mm. The body has a circumferential lip portion 42 extending radially outwardly from the body at the end thereof. A male alignment feature 44, configured as an elongated tab extending in a longitudinal direction, extends radially inwardly from an interior surface of the inlet end 20 into the expansion chamber 40. In an alternative embodiment, the alignment feature may be female, formed for example as a channel or groove.

The outlet end 22 of the body includes a substantially cylindrical first tubular portion 46 surrounding in part the interior cavity 14 and inhalation outlet 12, and a second substantially cylindrical or second tubular portion 48 surrounding the first tubular portion and defining an annular channel 50 or cavity. It should be understood that the tubular portions 46, 48 may have other non-cylindrical shapes, including for example and without limitation polygonal, elliptical, obround, triangular, etc. cross-sections. The body 4 has a lip portion 52 extending radially outwardly from, and circumferentially around, the body at an intermediate portion thereof, being positioned for example longitudinally downstream of the orifice outlet 34. The lip may extend only partially around the circumference of the body, thereby defining an opening 54. A female alignment feature 56, configured as a longitudinally extending channel or groove, is formed in the first tubular portion and extends inwardly from the end of the inlet end. In an alternative embodiment, the alignment feature may be male, configured for example as an elongated tab extending in a longitudinal direction, while also extending radially inwardly into the expansion chamber. The first tubular portion further includes a catch member 58, configured for example as a tab extending radially inwardly from the interior surface.

The inner surface of the body 4 defining the interior cavity has a annular convexly shaped shoulder 60, which narrows the interior cavity downstream from the expansion chamber 40 to define at least in part a multiplier area 62 adjacent and at least partially circumferentially surrounding the orifice outlet 34. For example, the interior cavity 14 may have an inner diameter of 10.32 mm adjacent the orifice outlet 34.

The baffle insert 6 includes a sound reducer baffle 64, having a convex dome surface 66 spaced apart and facing the outlet orifice 34 of the fluid inlet when the baffle insert is coupled to the body. In one embodiment, the distance between the baffle and the orifice is 3.15±0.5 mm. In one embodiment, the dome is semi-spherical and has a diameter of 3.6±0.01 mm. A plurality (shown as two) of spokes 68 position the baffle 64 in a flow channel 70 defined by the baffle insert and aligned with and defining the first longitudinal axis 16, while providing openings 74 for air to pass around the baffle and flow toward the inhalation outlet 12. The baffle has a recess 72 on the back side extending into the baffle. It should be understood that the sound reducer baffle may be integrally formed with the body. In one embodiment, the baffle insert 6 is removably secured in the outlet end 22 of the body, with the baffle insert defining the inhalation outlet 12. An inlet end 76 of the baffle insert is shaped and narrows to define at least in part the multiplier area 62, with a venturi geometry 78 surrounding the outlet orifice 34, or positioned downstream therefrom. In one embodiment, the baffle insert is tubular, with a recess 80 formed in the inlet end 76 to surround and accommodate the head portion 28 of the fluid inlet. The baffle insert also includes a recess 82 shaped to receive the catch 58, or other detent, so as to removably secure the baffle insert to the body. The baffle insert may also, or alternatively, be secured by a friction fit, adhesives, or other types of fasteners. The baffle insert may also be fixedly secured to the body.

An exterior surface 84 of the tubular baffle insert engages the inner surface of the first tubular portion 46. A male alignment feature 86, configured as an elongated tab extending in a longitudinal direction, extends radially outwardly and is received in the female alignment feature 56. In an alternative embodiment, the alignment feature may be female, formed for example as a channel or groove. The alignment features interfaces with the alignment feature 56 on the body, ensuring that the recess 82 is aligned with the catch tab 58 for engagement. When the alignment features are aligned, the baffle insert may be secured to the body, and when the alignment features are not aligned, the baffle insert is not capable of being secured to the body. The baffle insert also includes a lip portion 87 extending radially outwardly, and circumferentially around, the tubular portion. The lip portion 87, shown as an enlarged cylindrical portion in the embodiment of FIG. 5B, engages the end 88 of the first tubular portion of the body to locate the baffle insert relative to the body in the longitudinal direction. The baffle insert defines a restrictor tube 92, which further defines the interior cavity 14 downstream of the baffle and the inhalation outlet thereof. The end of the restrictor tube preferably extends beyond the end of the body tubular portions in a downstream direction.

Figure 5A:
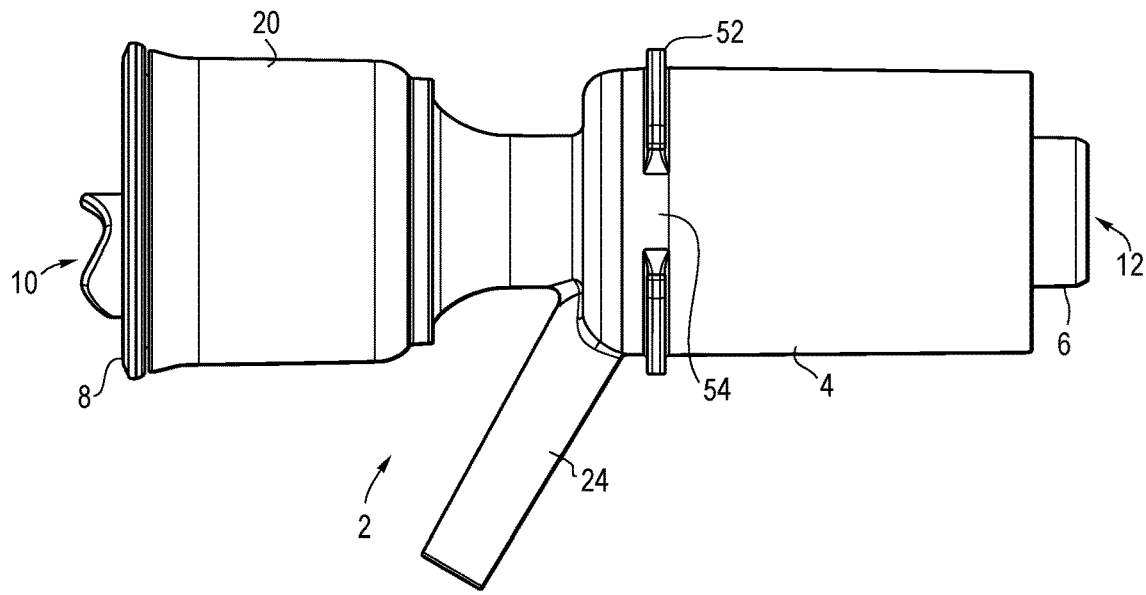
FIGS. 5A and 5B are side and cross-sectional views of the positive air pressure therapy device.
Figure 5B:
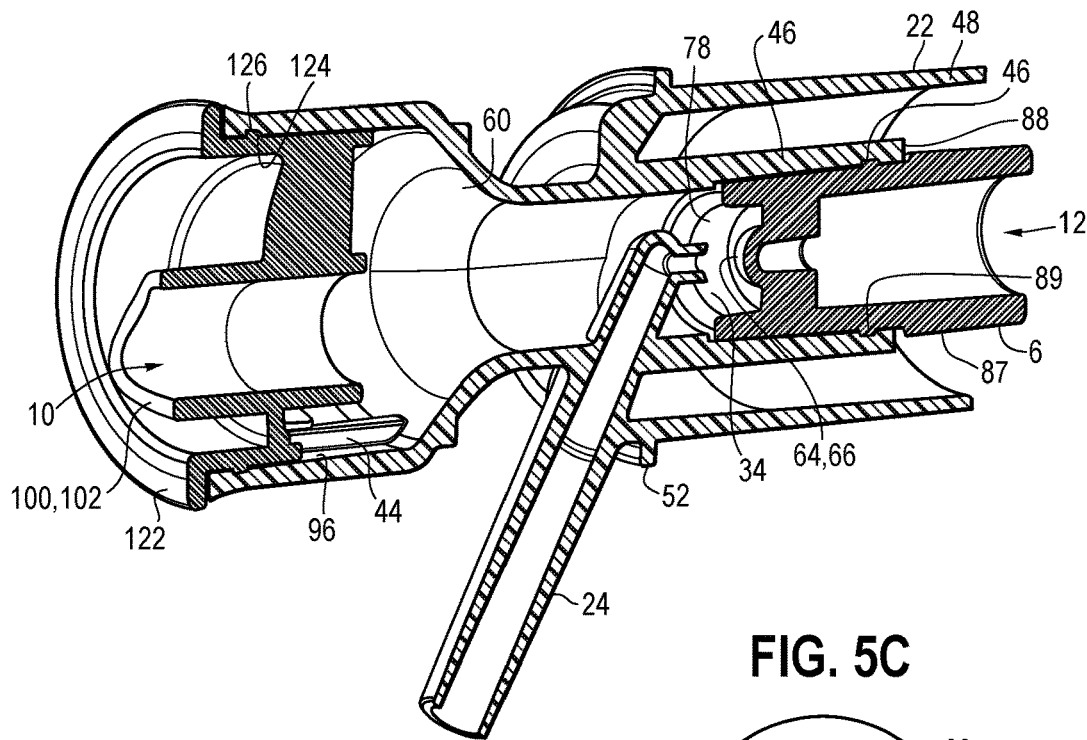

As shown in the embodiment of FIG. 5B, the baffle insert 6 may include a circumferential rib 89 that engages a corresponding groove in the tubular portion 46 of the body so as to locate and secure the baffle insert in the body.

The end cap 8 includes a circumferential wall 94 that is disposed interiorly of the cylindrical expansion chamber, with the wall defining an interior space of the expansion chamber 40. The end cap includes a recess or slot, or female alignment feature 96, which is shaped to receive the male alignment feature 44 of the body. In an alternative embodiment, the alignment feature may be male, formed for example as elongated tab or raised feature. When the alignment features are aligned, the end cap may be secured to the body, and when the alignment features are not aligned, the end cap is not capable of being secured to the body.

Figure 30:
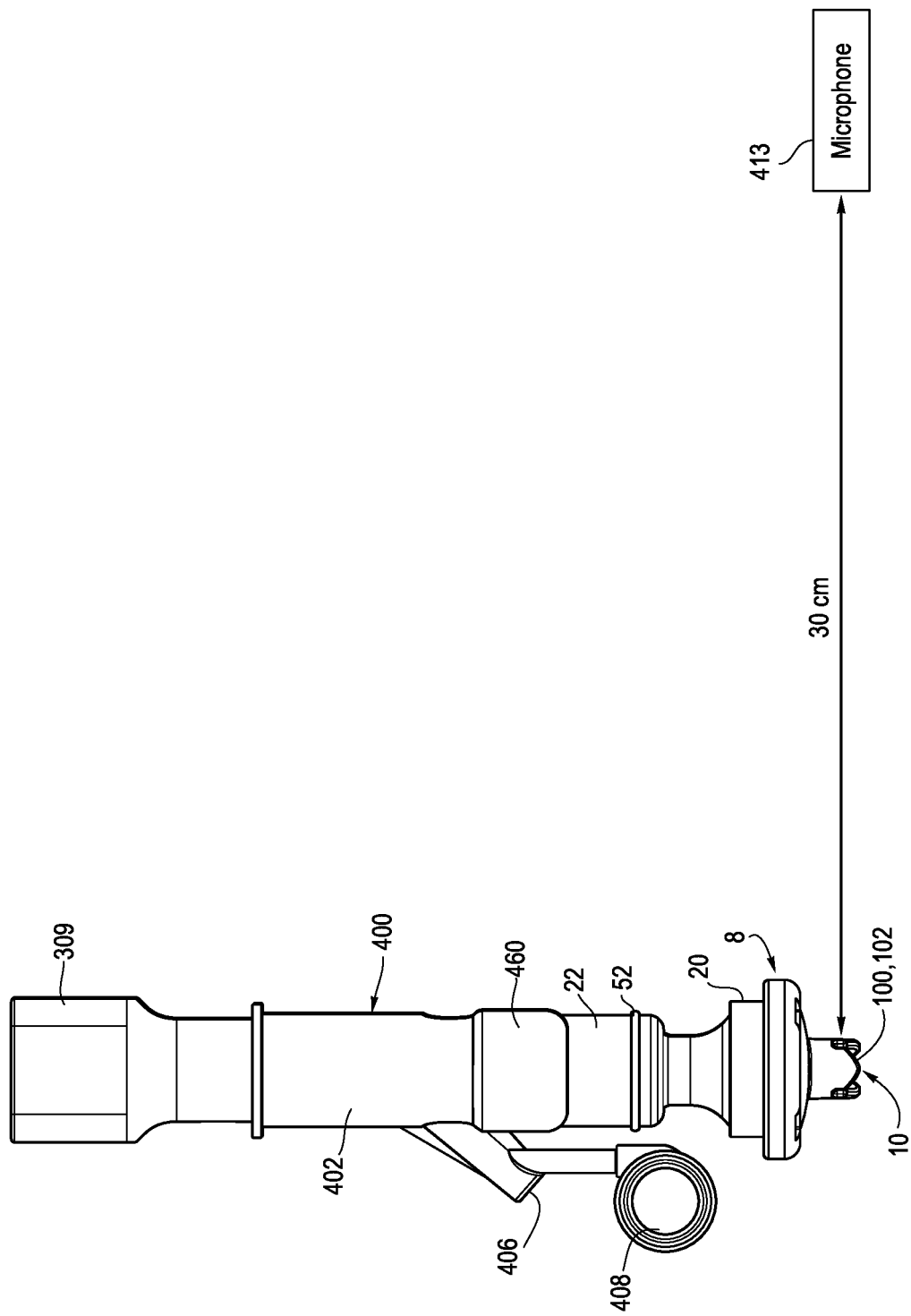
FIG. 30 shows a set-up for measuring the sound of the PAP.
Figure 33:
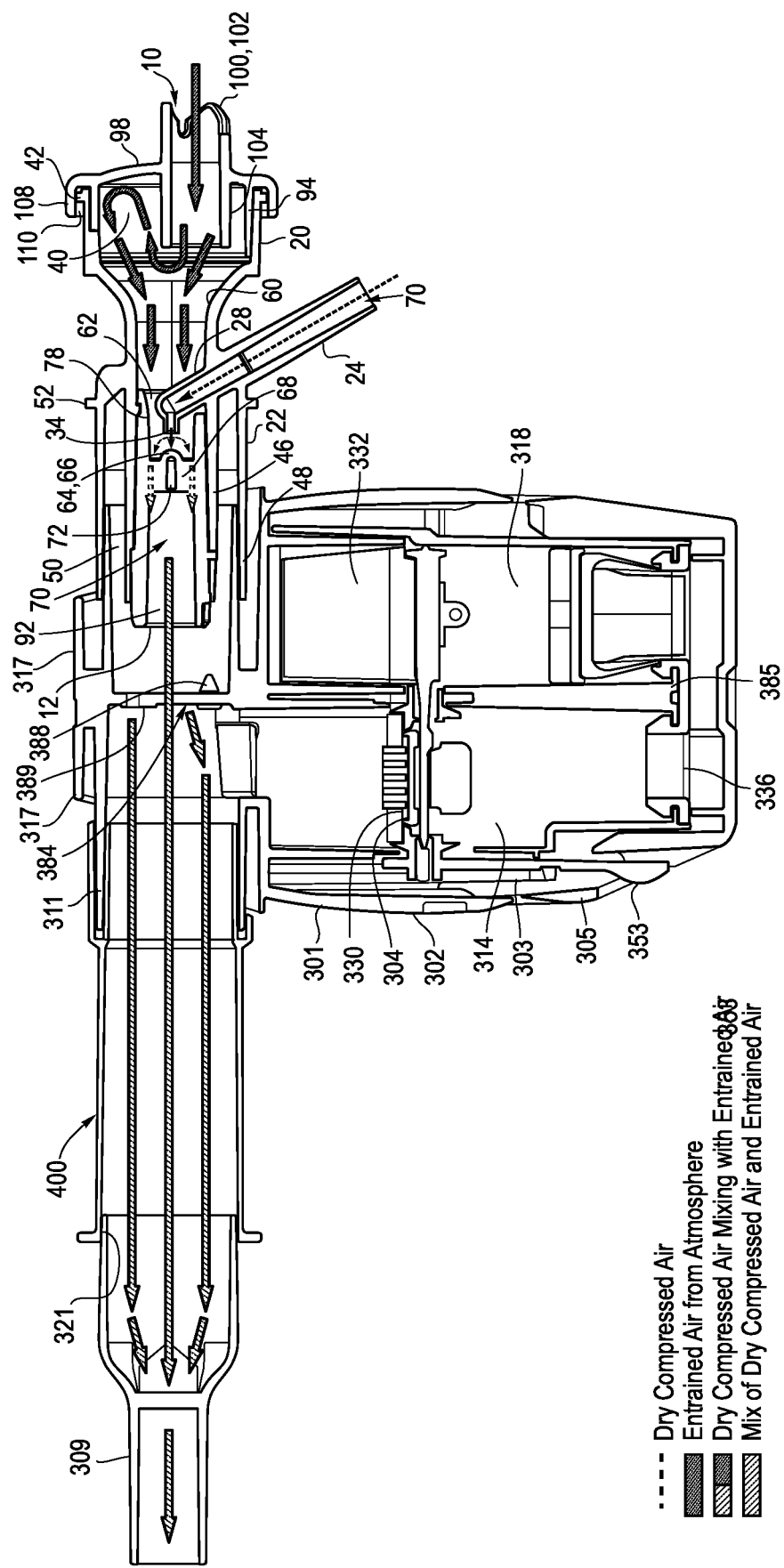
FIG. 33 is a cross-sectional view of the positive air pressure therapy device during inhalation when used in combination with OPEP.

The end cap has an end wall 98, with a tubular inlet 100 coupled thereto, with an exterior 102 extending longitudinally outwardly from the end wall 98 and an interior portion 104 extending longitudinally inwardly from the end wall. The interior portion has an outer surface 106, with an eccentric annular channel 108 defined around the outer surface and defining in part the expansion chamber 40. The tubular inlet 100 defines the inhalation inlet 10 and second longitudinal axis 18, which is offset from the first longitudinal axis 16 by distance D in one embodiment. The offset, (D) or eccentric muffler feature, diverts airflow through a tortuous path, which reduces the sound pressure wave peaks by way of sound reflection, with the frequency of the waves overlapping into cancelling some of the peaks, thereby reducing the overall noise level. In this way, an eccentric muffler feature (i.e., offset axes 16, 18) provides a quieter system than an end cap with aligned longitudinal axes. In one embodiment, the muffler feature provides for example a 2 to 3 dB nose level reduction as measured with a microphone 413 as shown in FIG. 30.

A second circumferential wall 109 extends from the end wall and defines an annular cavity or channel 110 between the walls. A plurality (shown as four) catch members 112 extend radially inwardly from the second wall and engage the lip portion of the body to releasably secure the end cap to the body. The end cap 8 may also, or alternatively, be secured by a friction fit, adhesives, or other types of fasteners.

Figure 28:
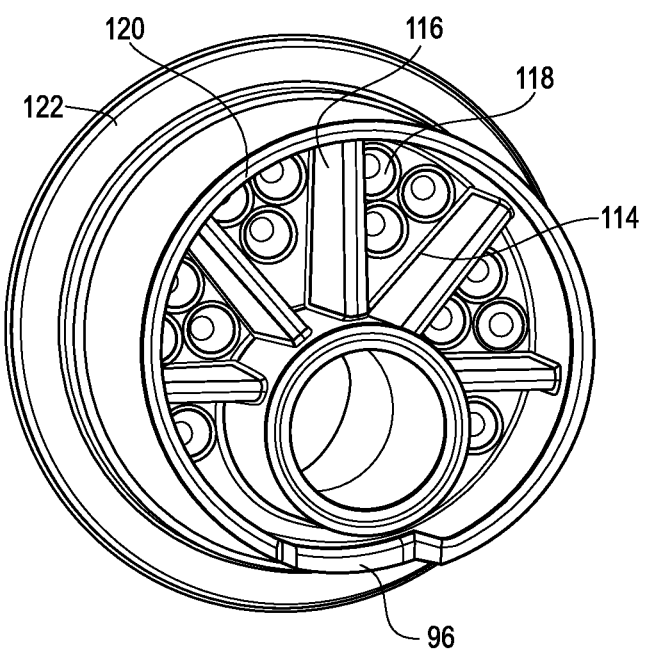
FIG. 28 is a front perspective view of one embodiment of an end cap.

Referring to the embodiment of FIGS. 5B and 28, the second wall is omitted, with the end cap having a circumferential flange 122, or lip, engaging the end of the body, with the an exterior catch member 124 engaging a recess 126 formed in the body to secure the end cap to the body. The interior surface 114 of the end wall may be configured with a plurality of ribs extending downstream therefrom and forming pie-shaped (sector) recesses 120, with the end wall having a plurality of dimples, recesses or indentations 118 disposed in each sector forming a honeycomb surface, with the ribs and honeycomb surface defining muffler features of the end cap. As set forth above, the muffler features may be incorporated into an end wall integrally formed as part of the body. It should be understood that in one embodiment, the end cap may be rotated about the axis 16, but with the eccentricity remaining the same.

Assembly and Kit

Referring to FIG. 2, the PAP device is assembled by inserting the end cap 8 into the inlet end 20 of the body, with the alignment features 44, 96 ensuring the proper orientation of the two components such that the catch feature or tabs 110, 124, may be engaged with the lip portion 42 or recess 126. The baffle insert 6 may be inserted into the outlet end 22 of the body, with the alignment features 56, 86 again ensuring the proper orientation of the two components such that the catch feature or tab 58 may be engaged with the recess 82.

Referring to FIGS. 1-4, the PAP device may be coupled to, and used in combination with, various therapy devices. For example, as shown in FIGS. 1-3, the inlet port 313 tubular portion of the OPEP 300 may be inserted into the annular channel 50 and engage an interior surface of the second tubular portion 48 of the outlet end of the PAP body, for example with a friction fit, or engage the exterior surface of the tubular portion 46.

Figure 4:
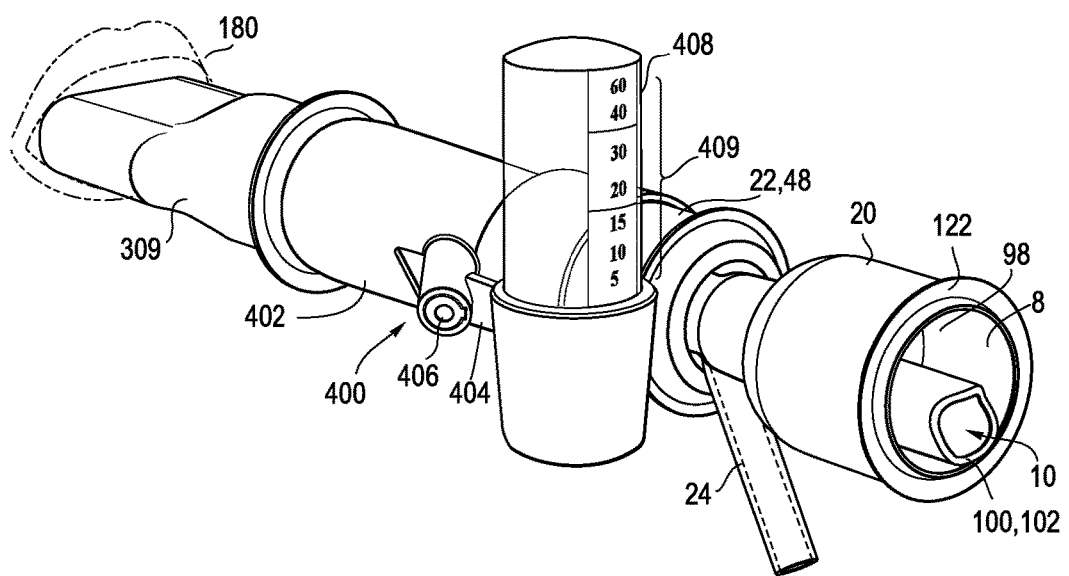
FIG. 4 is a perspective view of one embodiment of a positive air pressure therapy device coupled to a manometer.
Figure 10:
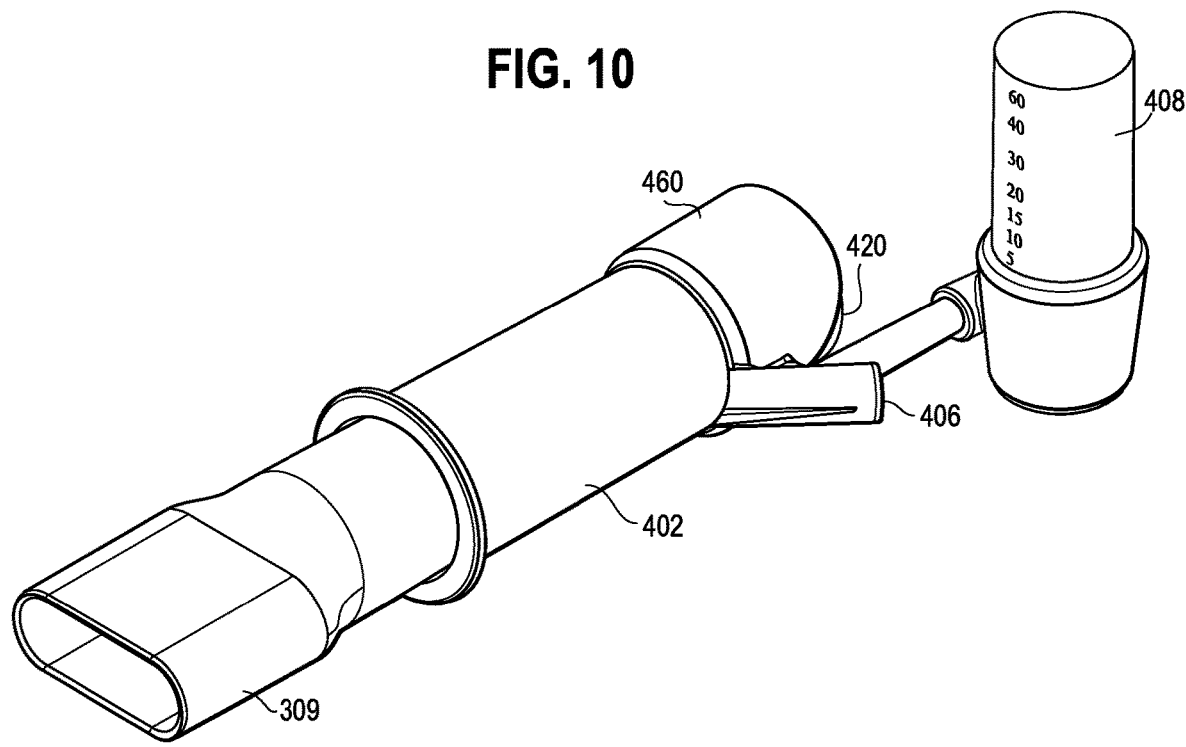
FIG. 10 is a perspective view of the manometer assembly shown in FIG. 9.
Figure 13:
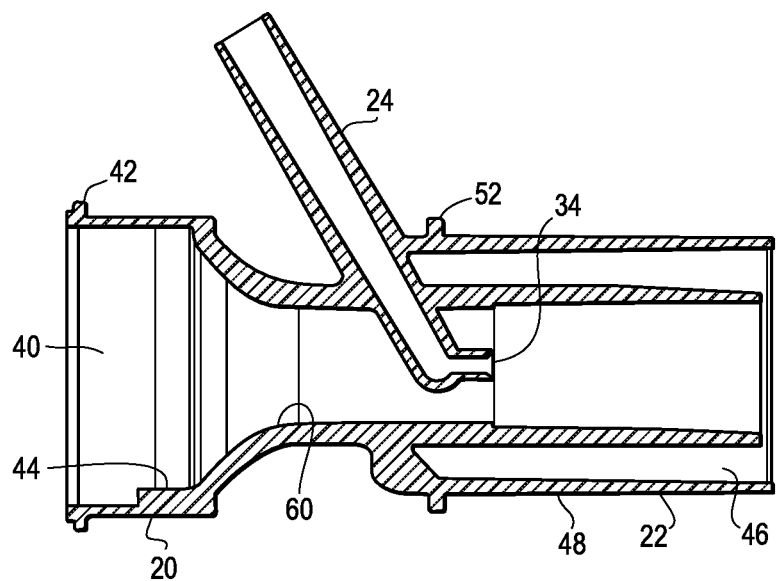
FIG. 13 is a cross-sectional view of the body component taken along line 13-13 of FIG. 12.
Figure 14:
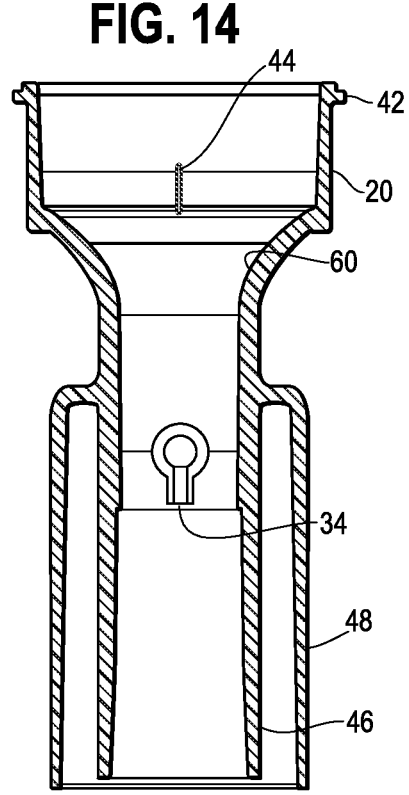
FIG. 14 is a cross-sectional view of the body component taken along line 14-14 of FIG. 12.
Figure 15:
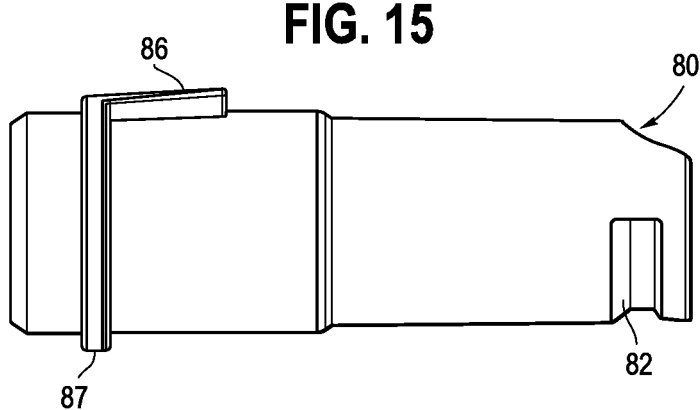
FIG. 15 is a side view of a baffle insert component of the positive air pressure therapy device shown in FIG. 6.
Figure 16:
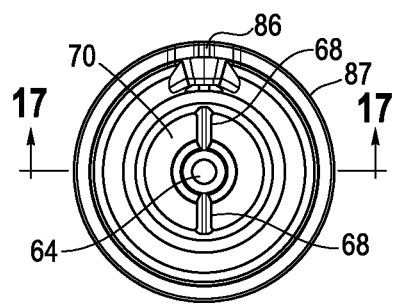
FIG. 16 is an end view of the baffle insert component of the positive air pressure therapy device shown in FIG. 15.
Figure 17:
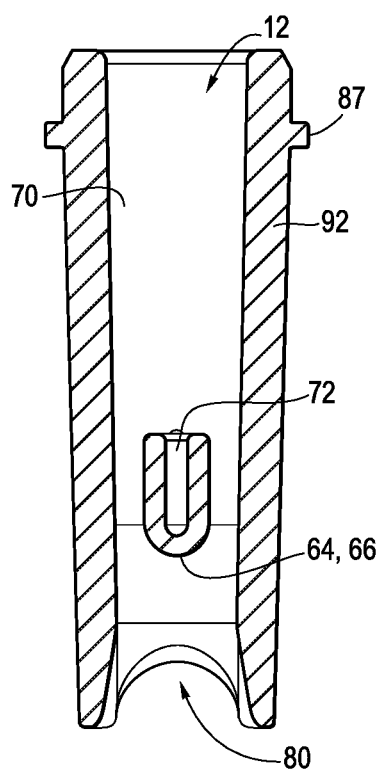
FIG. 17 is a cross-sectional view of the baffle insert component taken along line 17-17 of FIG. 16.
Figure 18:
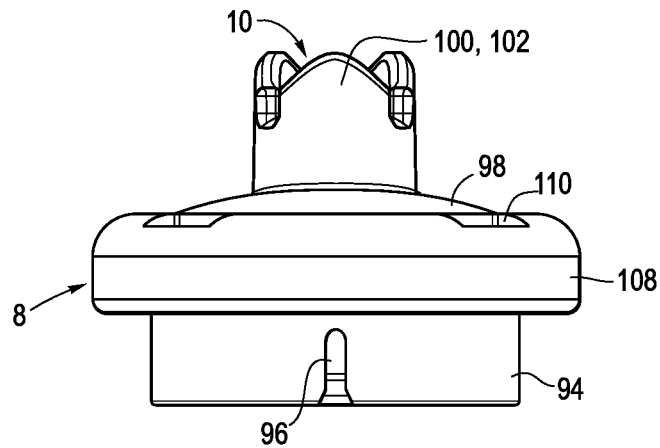
FIG. 18 is a side view of an end cap component of the positive air pressure therapy device shown in FIG. 6.
Figure 19:
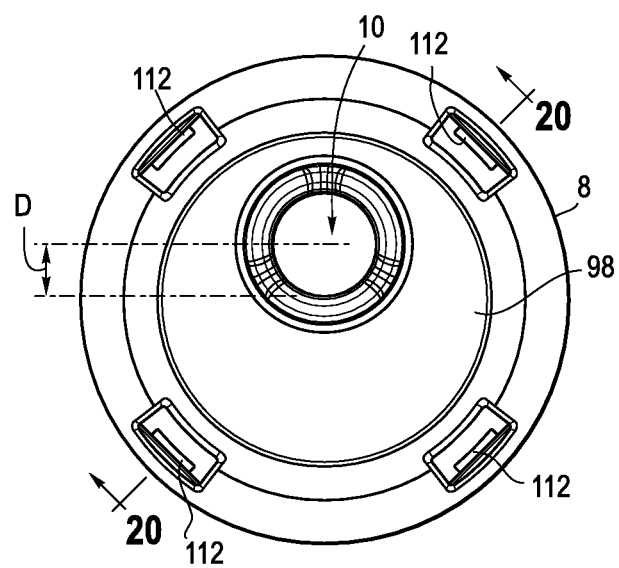
FIG. 19 is a rear view of the end cap component shown in FIG. 18.
Figure 20:
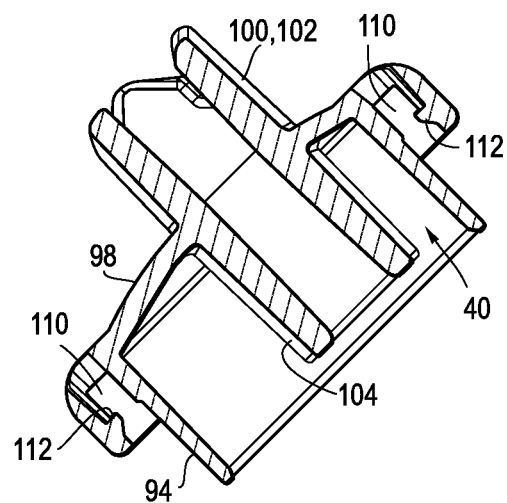
FIG. 20 is a cross-sectional view of the end cap component taken along line 20-20 of FIG. 19.

Referring to FIGS. 4, 9 and 10, the PAP device 2 may be coupled to the pressure indicator 400, again with a tubular portion 420 of the pressure indictor inserted into the annular channel 50 such that an exterior surface of the tubular potion 420 engages an interior surface of the second tubular portion 48 of the outlet end of the PAP body, for example with a friction fit, or engages the exterior surface of the tubular portion 46.

Figure 5C:
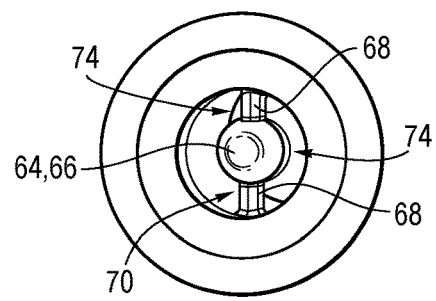
FIG. 5C is an enlarged perspective downstream view of the multiplier area and sound reducing dome.
Figure 6:
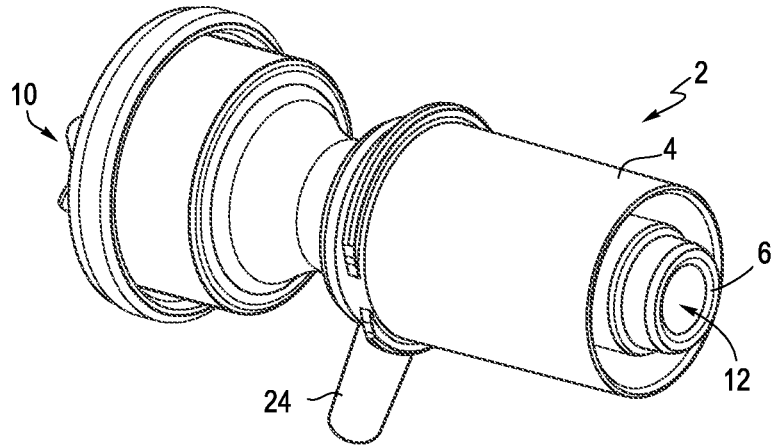
FIG. 6 is a perspective view of one embodiment of a positive air pressure therapy device.
Figure 7:
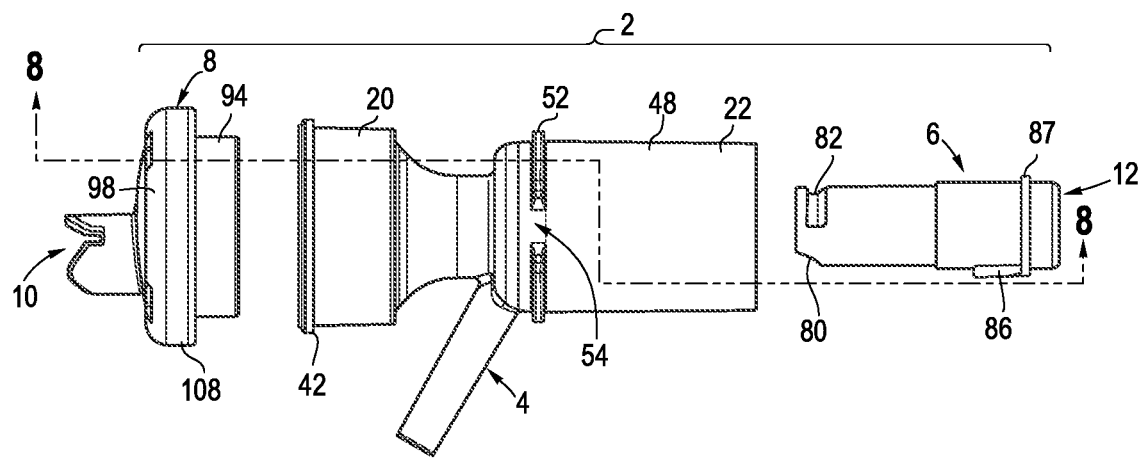
FIG. 7 is an exploded side view of the positive air pressure therapy device shown in FIG. 6.
Figure 8:
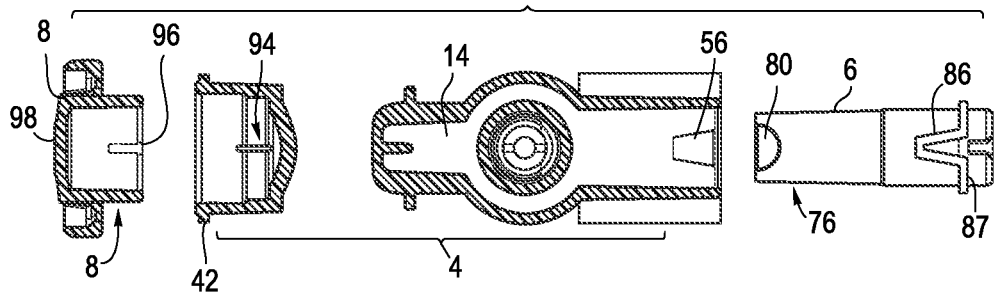
FIG. 8 is a cross-sectional view of the positive air pressure therapy device taken along line 8-8 of FIG. 7.

In yet another embodiment, shown in FIG. 5, the pressure indicator is coupled to the inhalation port 311 of the OPEP device, with the mouthpiece 309 then coupled to the outlet of the pressure indicator.

Operation

Referring to FIGS. 21-24 and 31-34, during patient inhalation, either directly through the inhalation outlet 12, or through a connected pressure indicator 400 and/or OPEP device 399, atmospheric air is drawn by the user 180 through the inhalation inlet 10 of the end cap 8 into the expansion chamber 40. The offset, or eccentric, muffler feature diverts airflow through a tortuous path, which reduces the sound pressure wave peaks by means of sound reflection and frequency waves overlapping into cancelling some of the peaks, thereby reducing the overall noise level. In this way, the eccentric muffler provides a quieter operation than an end cap with aligned axes, with a 2 to 3 dB nose level reduction., measured for example at a distance of 30 cm between the device and the caregiver, as shown in FIG. 30. The compressor or other pressurized fluid supply source 38 is actuated or turned on such that compressed fluid enters the flow path 30 and exits the orifice outlet 34 in a downstream direction, entraining and accelerating the air flow from the expansion chamber 40. The head portion 28 of the inlet functions as an orifice stabilizer, which reduces the fire hose effect that may cause unnecessary and unwanted vibrations and noise. The air flow from the expansion chamber 40 passes through the constricted venturi geometry 78, thereby increasing the velocity of the air flow.

Figure 24:
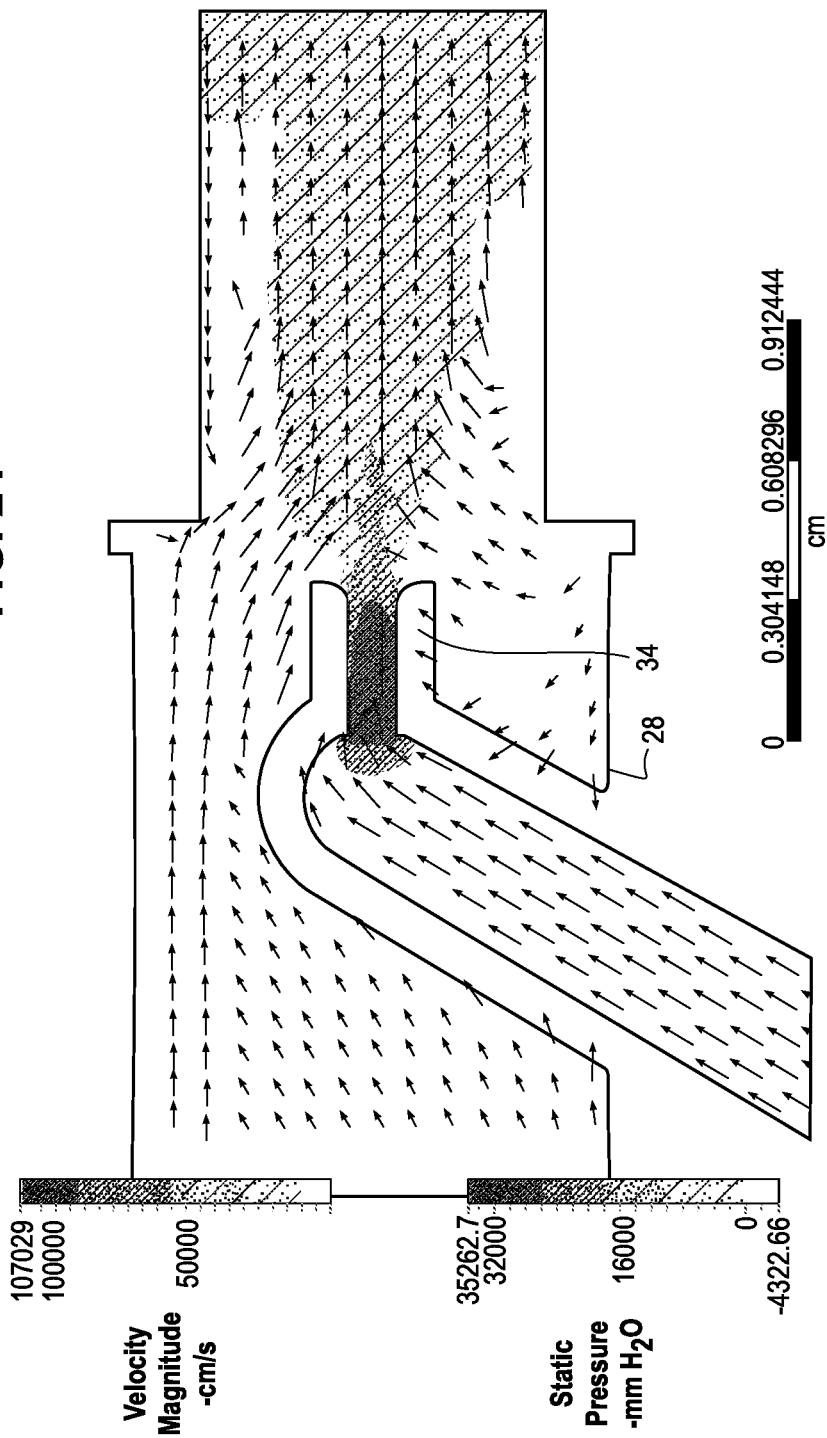
FIG. 24 is a color diagram showing noise producing vortexes during inhalation without a sound reducing baffle.
Figure 25:
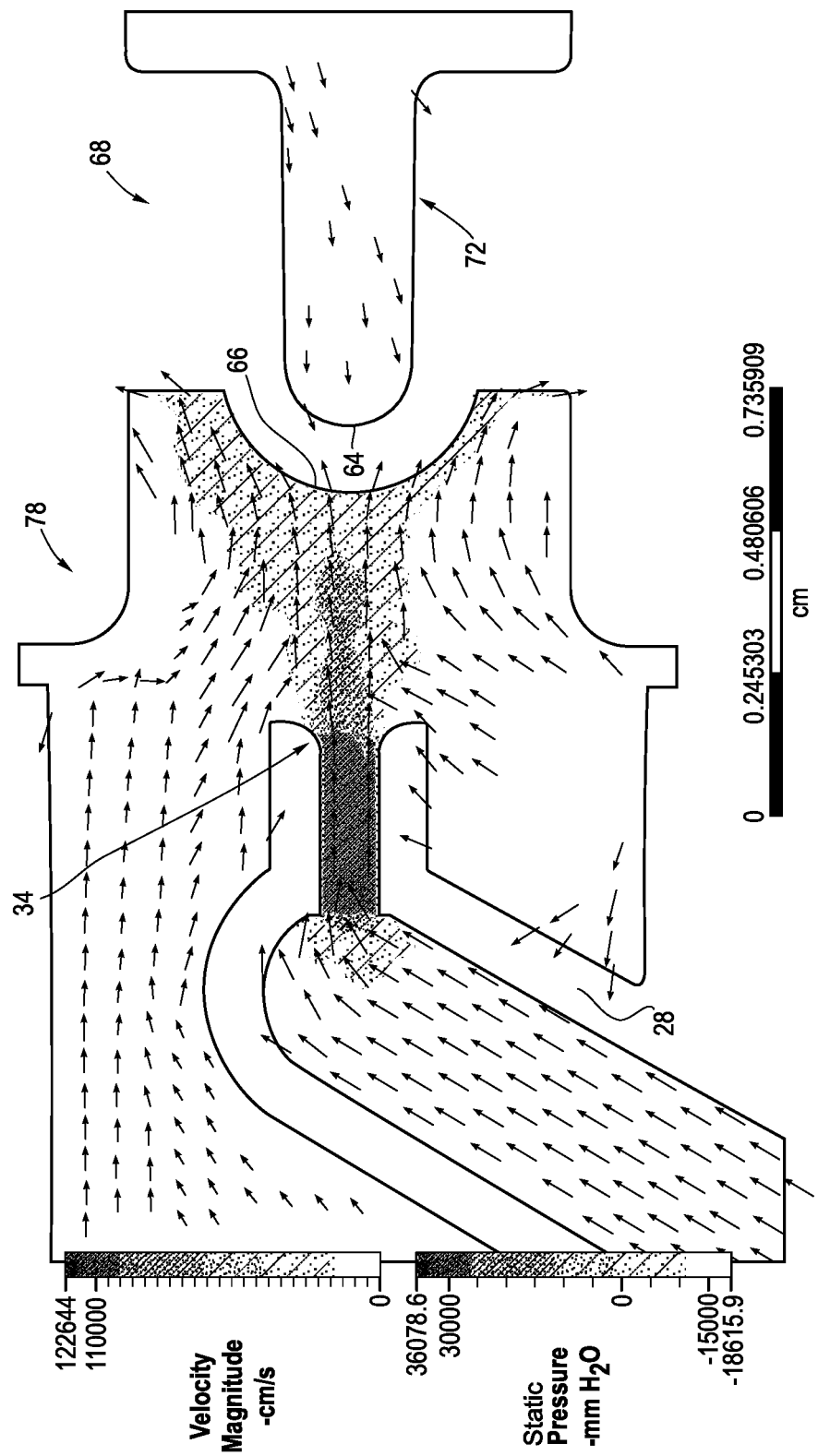
FIG. 25 is a color diagram showing noise producing vortexes during inhalation with a sound reducing baffle.
Figure 26:
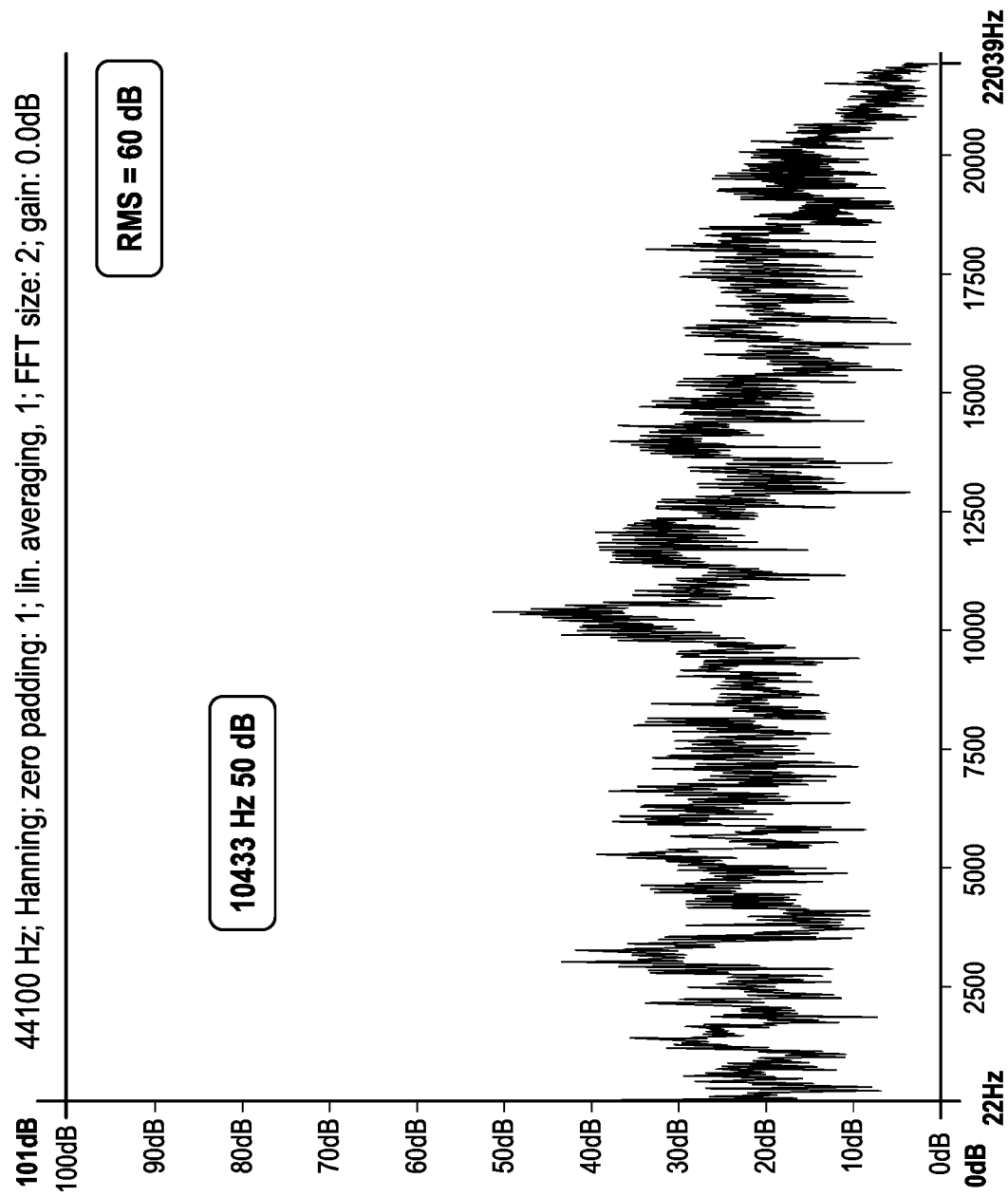
FIG. 26 is a sound pressure v. frequency graph for a device having a sound reducing baffle.
Figure 27:
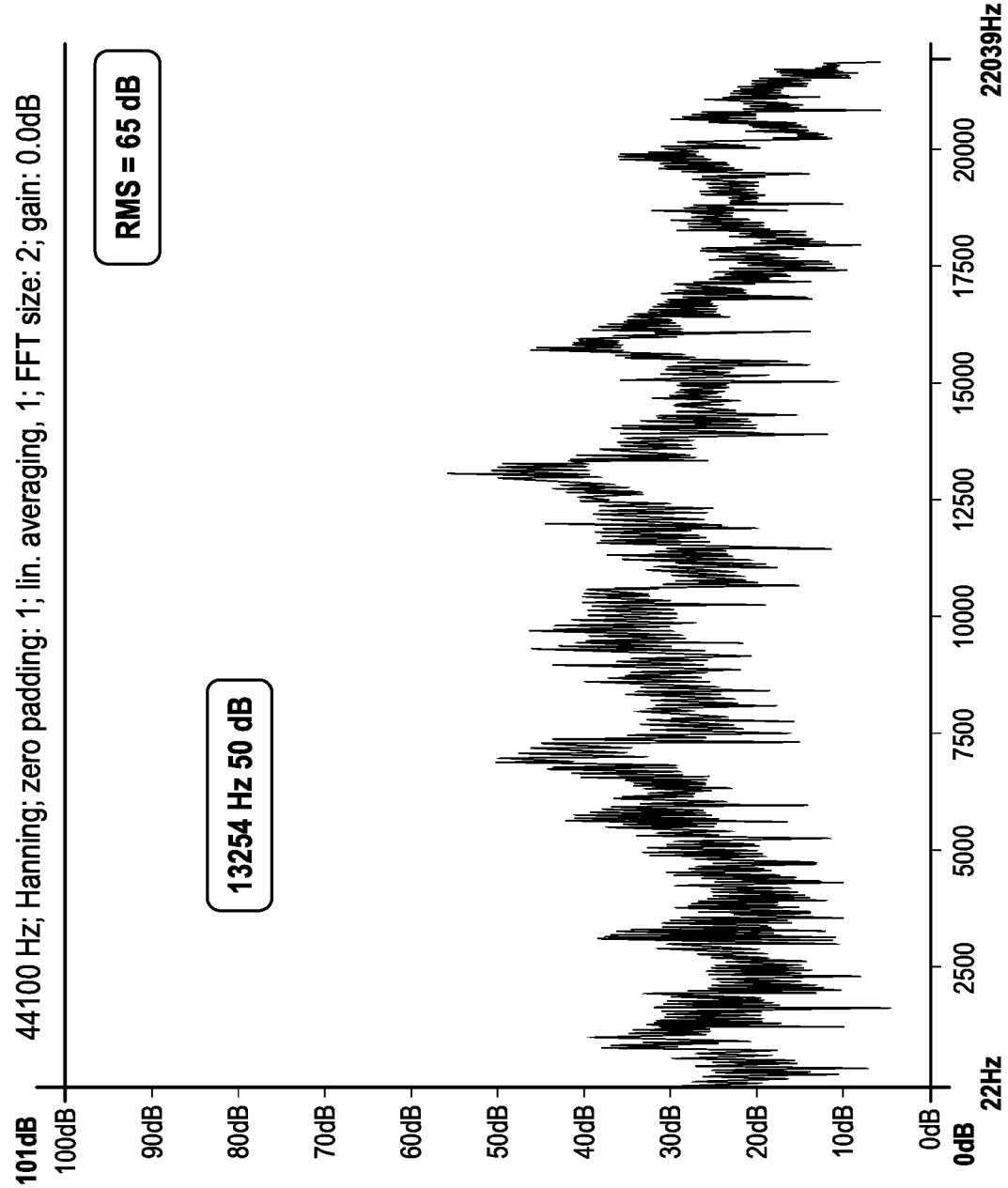
FIG. 27 is a sound pressure v. frequency graph for a device without a sound reducing baffle.

The pressurized fluid flow exiting the orifice outlet 34 is directed at the sound reducer baffle 64, with the dome surface 66 deflecting the flow around the dome and into the flow channel 70 of the restrictor tube and out the inhalation inlet 10. The fluid flow may then pass directly to the user, or through the OPEP device, by way of the one-way valve 384 and then to the user. Alternatively, the fluid flow may pass from the inhalation outlet 12 through the OPEP and the pressure indicator to the user, or from the inhalation outlet through the pressure indicator to the user. It should be understood that other therapy devices may also be used in combination with the PAP, including without limitation a nebulizer system. The sound reducer baffle 64, with dome surface 66, functions as an air streamlining baffle to the fluid flow, which reduces the air turbulence vortexes that are a source of sound due to air frequency vibrations. A comparison of the vortexes is shown in FIGS. 24 and 25, with the vortexes produced without a baffle shown in FIG. 24, and vortexes produced with the baffle shown in FGI. 25. As shown in FIGS. 26 and 27, the overall average sound of the PAP device 2 was reduced by 5 dB (at the location of the caregiver (microphone 413) as shown in FIG. 30), which may have a significant impact in the ability of the user and caregivers' ability to hear, which also creates a better patient experience and is less annoying to the patient and caregivers. The noise reduction is facilitated by both the sound reducer dome and muffler.

Figure 23:
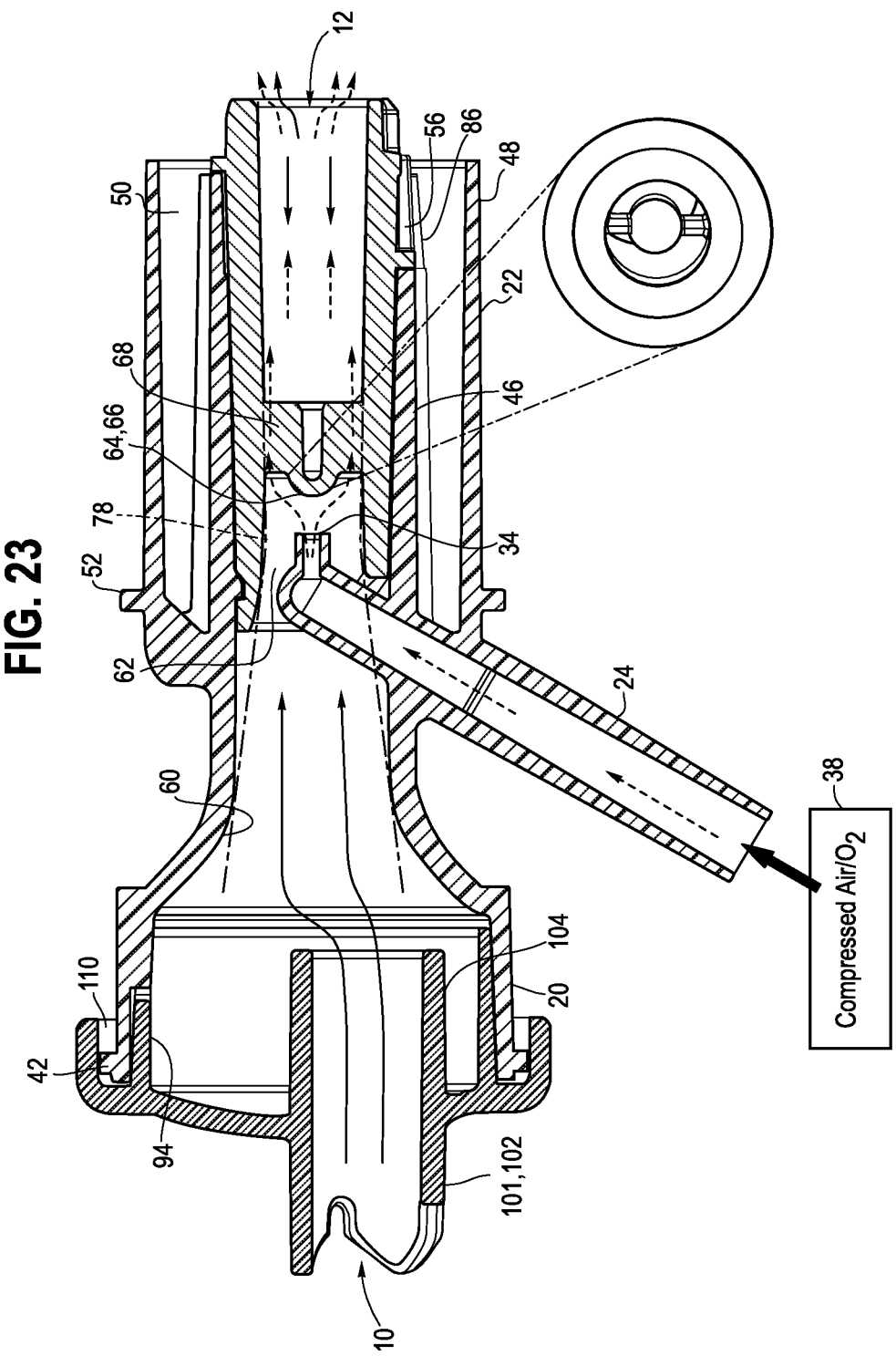
FIG. 23 is a cross-sectional view of the positive air pressure therapy device during exhalation when used in combination with OPEP.

When the PAP device 2 is used with the OPEP device 300, any exhalation air from the user that is introduced into the inhalation outlet encounters an air flow from the orifice outlet, as shown in FIGS. 23 and 34. Exhalation flow from the user through the mouthpiece and/or pressure indicator, and air flow from the PAP, exit through the OPEP device. The fluid flow of atmospheric air and compressed fluid from the outlet orifice may exit through the OPEP exhaust path. Some fluid flow may exit the inhalation inlet, depending on input pressures, which may help maintain elevated lung pressure when there is little or no exhalation flow.

Figure 22:
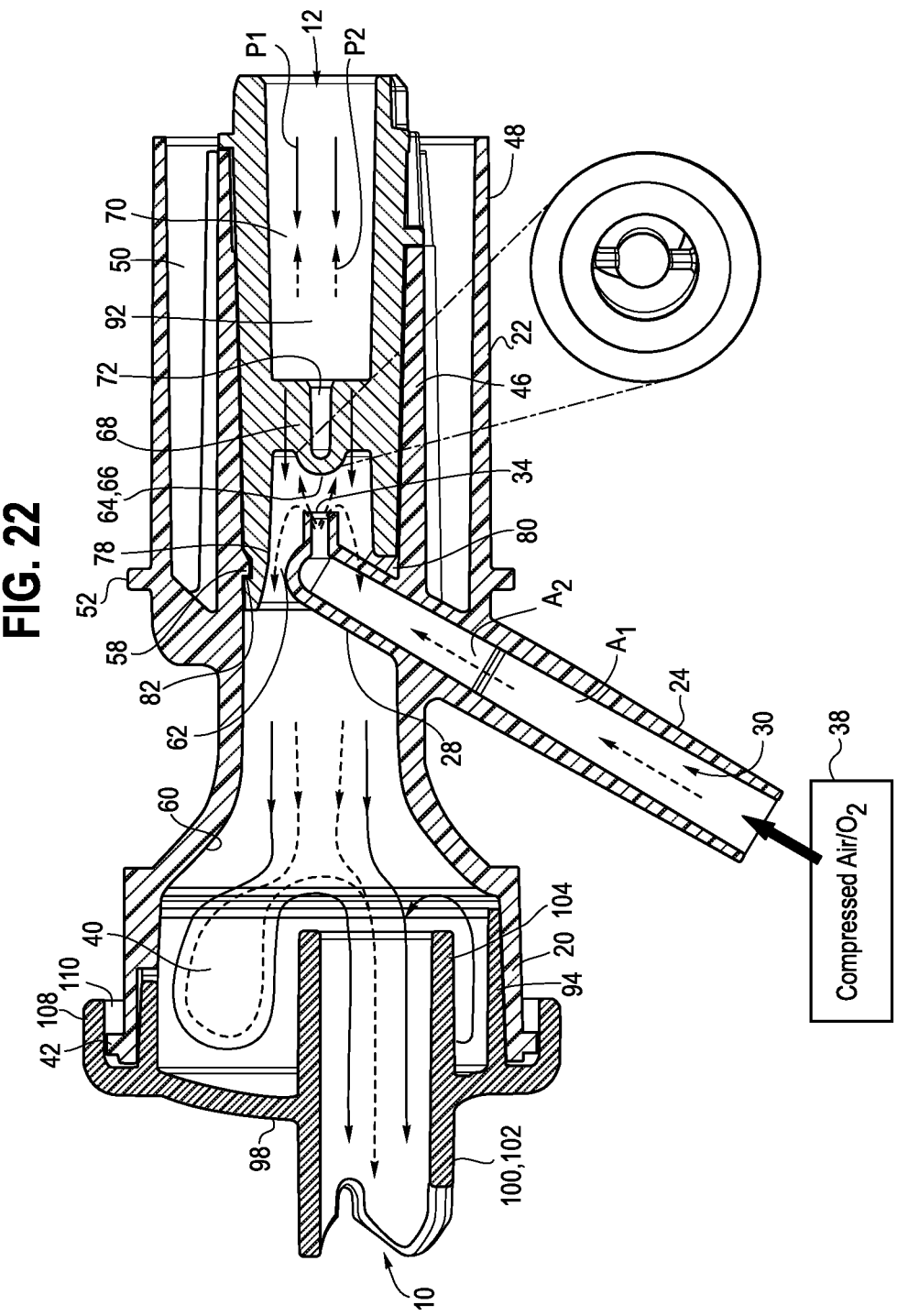
FIG. 22 is a cross-sectional view of the positive air pressure therapy device during exhalation when not used in combination with OPEP.
Figure 29:
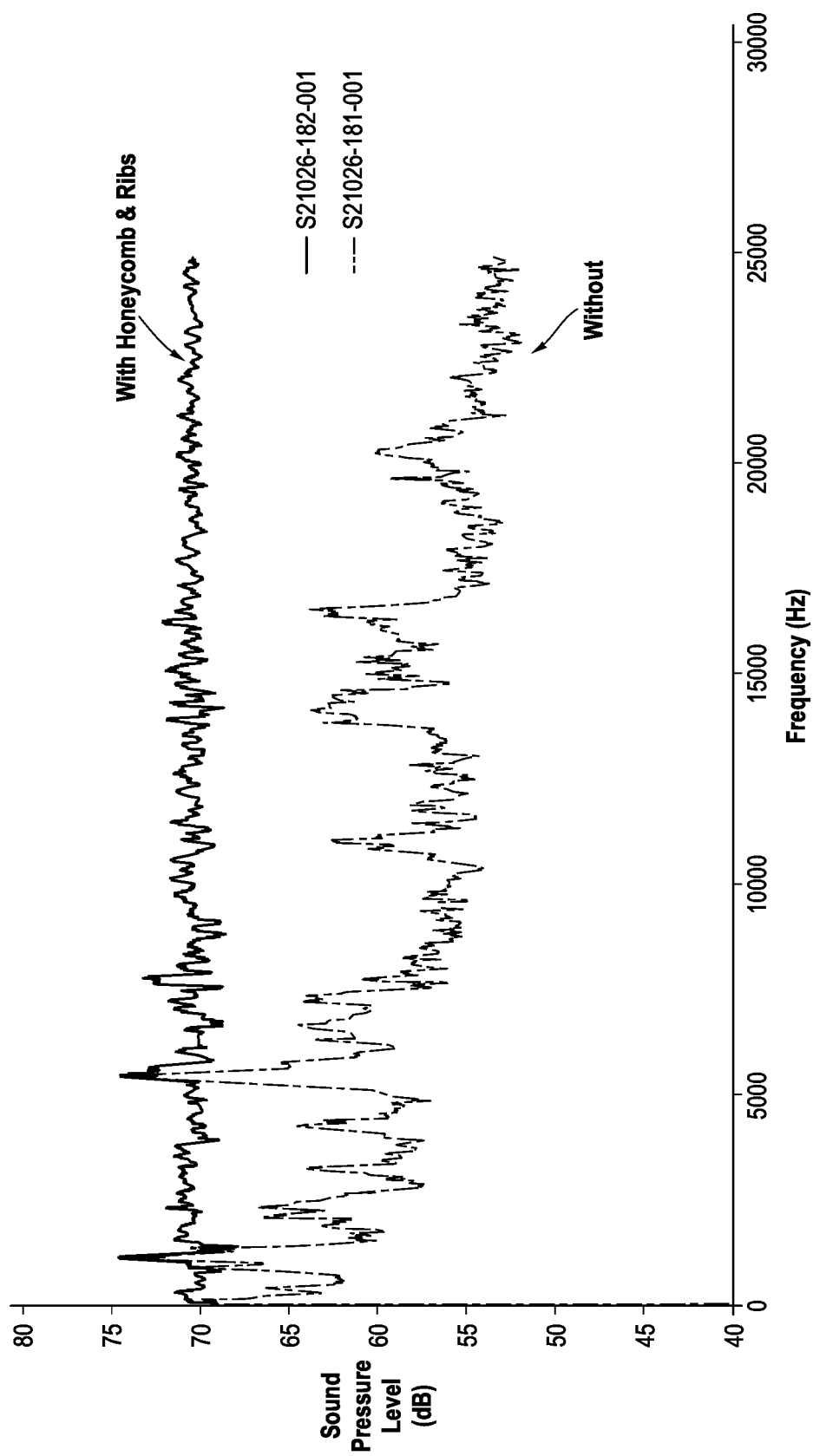
FIG. 29 is a sound pressure v. frequency graph comparing a device configured with and without a sound reducing end cap.

Referring to FIGS. 22 and 32, when there is no OPEP device coupled to the PAP, for example when used alone or in combination with the pressure indicator, exhaled air enters the inhalation outlet 12, facing off with the compressed fluid flow from the orifice outlet 34, creating a pressure buildup. The majority of the flow passes back through the interior cavity 14 into the expansion chamber 40 and then out of the inhalation inlet 10. This helps maintain elevated lung pressure when there is little or no exhalation flow. During inhalation or exhalation, the muffler features, including the ribs 116 and honeycomb structure 118, average out the sound amplitude peaks and valleys into a smother overall average, which provides for a more consistent sound level average as shown in FIG. 29, while being maintained below 80 dB.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A positive air pressure delivery device comprising:
   a housing comprising:
      an inhalation inlet;
      an inhalation outlet; and
      an interior cavity in fluid communication with the inhalation inlet and outlet;
   a pressurized fluid inlet comprising an outlet orifice in fluid communication with the interior cavity between the inhalation inlet and outlet; and
   a sound reducer baffle having a convex dome surface positioned downstream of, facing and in-line with the outlet orifice in a spaced apart relationship therewith, wherein the outlet orifice is adapted to direct a fluid flow toward the dome surface.

2. The positive air pressure device of claim 1 wherein the housing comprises a body having an inlet end and an outlet end, wherein the pressurized fluid inlet is coupled to the body, and an end cap is secured in the inlet end, wherein the end cap defines the inhalation inlet.

3. The positive air pressure device of claim 2 wherein the end cap is removeably secured in the inlet end.

4. The positive air pressure device of claim 2 wherein the body comprises a first alignment feature and the end cap comprises a second alignment feature, wherein the first and second alignment features are aligned when the end cap is secured in the inlet end.

5. The positive air pressure device of claim 2 further comprising a baffle insert comprising the sound reducer baffle, wherein the baffle insert is secured in the outlet end, wherein the baffle insert defines the inhalation outlet.

6. The positive air pressure device of claim 5 wherein the baffle insert is removeably secured in the outlet end.

7. The positive air pressure device of claim 5 wherein the body comprises a first alignment feature and the baffle insert comprises a second alignment feature, wherein the first and second alignment features are aligned when the baffle insert is secured in the outlet end.

8. The positive air pressure device of claim 5 wherein the baffle insert defines a multiplier chamber surrounding the orifice outlet upstream of the sound reducer baffle.

9. The positive air pressure device of claim 5 wherein the baffle insert comprises a tubular member defining a flow channel, wherein the baffle is disposed in the flow channel and coupled to the tubular member with a plurality of spokes, wherein the plurality of spokes defines a plurality of openings between the plurality of spokes, wherein the plurality of openings are adapted to let air flow between the plurality of spokes.

10. The positive air pressure device of claim 2 wherein the inhalation inlet defines a first axis, and wherein the inhalation outlet defines a second axis, wherein the first and second axes are not coaxial.

11. The positive air pressure device of claim 10 wherein the first and second axes are parallel.

12. The positive air pressure device of claim 10 wherein the inhalation inlet is at least partially surrounded by an expansion chamber defined by the end cap.

13. The positive air pressure device of claim 12 wherein the expansion chamber has an end wall configured with muffler features.

14. The positive air pressure device of claim 13 wherein the muffler features comprise a plurality of ribs and/or indentations.

15. The positive air pressure device of claim 1 wherein said interior cavity defines a venturi surrounding the outlet orifice.

16. The positive air pressure device of claim 1 wherein the body comprises a first tubular portion defining an annular cavity surrounding the inhalation outlet.

17. The positive air pressure device of claim 16 further comprising a therapy device having a second tubular portion, wherein the second tubular portion is adapted to interface with the first tubular portion.

18. The positive air pressure device of claim 17 wherein the second tubular portion is received in the annular cavity.

19. The positive air pressure device of claim 17 wherein the therapy device comprises an oscillating positive expiratory pressure device.

20. The positive air pressure device of claim 17 wherein the therapy device comprises a pressure indicating device.

21. The positive air pressure device of claim 1 wherein the outlet orifice is oriented in a downstream direction away from the inhalation inlet and toward the inhalation outlet.

22. A positive air pressure assembly kit comprising:
   a body comprising;
      an inlet end;
      an outlet end;
      an interior cavity in fluid communication with the inlet and outlet ends; and
      a pressurized fluid inlet comprising an outlet orifice in fluid communication with the interior cavity between the inlet and outlet ends;
   an end cap adapted to be coupled to the inlet end, the end cap defining an inhalation inlet adapted to open into the interior cavity; and
   a baffle insert adapted to be coupled to the outlet end, the baffle insert comprising a sound reducer baffle having a convex dome surface adapted to be positioned downstream of, facing and in-line with the outlet orifice in a spaced apart relationship therewith when the baffle insert is coupled to the outlet end, the baffle insert further comprising an inhalation outlet.

23. The positive air pressure assembly kit of claim 22 wherein the body comprises a first alignment feature and the end cap comprises a second alignment feature, wherein when the first and second alignment features are aligned, the end cap may be secured to the body, and wherein when the first and second alignment features are not aligned, the end cap is not capable of being secured to the body.

24. The positive air pressure assembly kit of claim 22 wherein the body comprises a first alignment feature and the baffle insert comprises a second alignment feature, wherein when the first and second alignment features are aligned, the baffle insert may be secured to the body, and wherein when the first and second alignment features are not aligned, the baffle insert is not capable of being secured to the body.

25. The positive air pressure assembly kit of claim 22 wherein baffle insert defines a venturi adapted surrounding the outlet orifice.

26. The positive air pressure assembly kit of claim 22 wherein the body comprises a first tubular portion defining an annular cavity surrounding the inhalation outlet, and further comprising a therapy device having a second tubular portion, wherein the second tubular portion is adapted to interface with the first tubular portion.

27. The positive air pressure assembly kit of claim 26 wherein the therapy device comprises an oscillating positive expiratory pressure device.

28. The positive air pressure assembly kit of claim 26 wherein the therapy device comprises a pressure indicating device.

29. The positive air pressure assembly kit of claim 22 wherein the inhalation inlet defines a first axis, and wherein the inhalation outlet defines a second axis, wherein the first and second axes are not coaxial when the end cap and baffle inserts are coupled to the body.

30. The positive air pressure assembly kit of claim 22 wherein the end cap defines an expansion chamber at least partially surrounding the inhalation inlet.

31. The positive air pressure assembly kit of claim 30 wherein the end cap has an end wall configured with muffler features.

32. The positive air pressure assembly kit of claim 31 wherein the muffler features comprise a plurality of ribs and/or indentations.

33. The positive air pressure assembly kit of claim 22 wherein the outlet orifice is oriented in a downstream direction away from the inlet end and toward the outlet end.

34. The positive air pressure assembly kit of claim 22 wherein the body is a one-piece unitary member.

35. The positive air pressure assembly kit of claim 22 wherein the baffle insert comprises a tubular member defining a flow channel, wherein the baffle is disposed in the flow channel and coupled to the tubular member with a plurality of spokes, wherein the plurality of spokes defines a plurality of openings between the plurality of spokes, wherein the plurality of openings are adapted to let air flow between the plurality of spokes.

36. A method of administering a positive air pressure to a user comprising:
- passing air through an inhalation inlet of a housing into an interior cavity of the housing;
- introducing a pressurized fluid into the interior cavity through an outlet orifice of a pressurized fluid inlet and thereby accelerating the air in the interior cavity of the housing;
- impacting a convex dome surface of a sound reducer baffle with the pressurized fluid, wherein the convex dome surface is positioned downstream of, facing and in-line with the outlet orifice in a spaced apart relationship therewith; and
- passing the air and the pressurized fluid through an inhalation outlet.

37. The method of claim 36 further comprising passing the air and pressurized fluid between a plurality of spokes holding the baffle in a flow channel prior to the passing the air and the pressurized fluid through the inhalation outlet.

\* \* \* \* \*